United States Patent
Yang et al.

(10) Patent No.: US 10,350,602 B2
(45) Date of Patent: Jul. 16, 2019

(54) DEVICES FOR SEPARATING CONSTITUENTS IN A SAMPLE AND METHODS FOR USE THEREOF

(71) Applicant: The Regents of the University of California, Oakland, CA (US)

(72) Inventors: Daniel K. Yang, Berkeley, CA (US); Lydia Lee Sohn, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 176 days.

(21) Appl. No.: 15/323,267

(22) PCT Filed: Jun. 30, 2015

(86) PCT No.: PCT/US2015/038656
§ 371 (c)(1),
(2) Date: Dec. 30, 2016

(87) PCT Pub. No.: WO2016/004101
PCT Pub. Date: Jan. 7, 2016

(65) Prior Publication Data
US 2018/0200717 A1    Jul. 19, 2018

Related U.S. Application Data

(60) Provisional application No. 62/020,279, filed on Jul. 2, 2014, provisional application No. 62/155,363, filed on Apr. 30, 2015.

(51) Int. Cl.
*B01L 3/00* (2006.01)
*F15D 1/14* (2006.01)
(Continued)

(52) U.S. Cl.
CPC ... *B01L 3/502776* (2013.01); *B01L 3/502761* (2013.01); *F15D 1/14* (2013.01);
(Continued)

(58) Field of Classification Search
CPC ..... B01L 2200/0652; B01L 2300/0654; B01L 2300/0864; B01L 2300/123; B01L 2400/086; B01L 3/502761; B01L 3/502776; F15D 1/14; G01N 15/0255; G01N 2015/0288; G01N 33/56972
See application file for complete search history.

(56) References Cited

U.S. PATENT DOCUMENTS

| 7,279,883 B2 | 10/2007 | Sohn et al. |
| 2009/0014360 A1 | 1/2009 | Toner et al. |

(Continued)

FOREIGN PATENT DOCUMENTS

| WO | 2013049404 | 4/2013 |
| WO | 2013052890 | 4/2013 |
| WO | 2014150928 | 9/2014 |

OTHER PUBLICATIONS

Kuntaegowdanahalli et al., (2009) "Inertial microfluidics for continuous particle separation in spiral microchannels," Lab Chip 9: 2973-2980.
(Continued)

*Primary Examiner* — John Kim
(74) *Attorney, Agent, or Firm* — Rudy J. Ng; Bozicevic, Field & Francis LLP

(57) ABSTRACT

Devices for separating constituents (e.g., cells) in a fluid sample are provided. The device includes a microfluidic conduit configured to carry a flow of a fluid sample and includes two or more separation elements, each separation element including a first region and a second region, where the first region has a cross-sectional area less than a cross-sectional area of the second region. The device also includes a flow resistive element in fluid communication with the microfluidic conduit in a region between two adjacent separation elements. Also provided are methods of using the devices, as well as systems and kits that include the devices. The devices, systems, methods and kits find use in a variety of different applications, including diagnostic assays.

38 Claims, 31 Drawing Sheets

(51) Int. Cl.
*G01N 15/02* (2006.01)
*G01N 33/569* (2006.01)

(52) U.S. Cl.
CPC ... *G01N 15/0255* (2013.01); *G01N 33/56972* (2013.01); *B01L 2200/0652* (2013.01); *B01L 2300/0654* (2013.01); *B01L 2300/0864* (2013.01); *B01L 2300/123* (2013.01); *B01L 2400/086* (2013.01); *G01N 2015/0288* (2013.01)

(56) References Cited

U.S. PATENT DOCUMENTS

| | | |
|---|---|---|
| 2009/0325276 A1 | 12/2009 | Battrell et al. |
| 2011/0070581 A1 | 3/2011 | Gupta et al. |
| 2012/0103903 A1 | 5/2012 | Hill et al. |
| 2013/0130226 A1 | 5/2013 | Lim et al. |

OTHER PUBLICATIONS

Lee et al., (2010) "Inertial separation in a contraction-expansion array microchannel," Journal of Chromatography A 1218(27):4138-4143.

Lee et al., (2013) "Label-Free Cancer Cell Separation from Human Whole Blood Using Inertial Microfluidics at Low Shear Stress," Anal. Chem. 85: 6213-6218.

Zhang et al., (2013) "Inertial focusing in a straight channel with asymmetrical expansion-contraction cavity arrays using two secondary flows," Journal of Micromechanics and Microengineering 23(8): 1-13.

DEVICES FOR SEPARATING CONSTITUENTS IN A SAMPLE AND METHODS FOR USE THEREOF

CROSS-REFERENCE TO RELATED APPLICATIONS

Pursuant to 35 U.S.C. § 119(e), this application claims priority to the filing date of U.S. Provisional Application No. 62/020,279, filed Jul. 2, 2014, and U.S. Provisional Application No. 62/155,363, filed Apr. 30, 2015, the disclosures of each of which are incorporated herein by reference.

INTRODUCTION

Cell characterization is used in cell biology for disease diagnosis and monitoring, and drug discovery. Although current methods for cell analysis, such as flow cytometry and magnetic-bead column selection have been used in both research laboratories and clinical settings, improved devices and methods may be desirable. For example, traditional approaches often require advanced preparation, including exogenous labeling of cells. Such labeling leads to added incubation time, additional costs, loss of sample, and the possibility of modifying cell physiology and function. In addition, traditional approaches do not lend themselves to portability, which can be desirable in certain clinical situations.

Circulating tumor cells (CTCs) are cells that have been shed from primary solid tumors and have entered into the blood stream. They are believed to play a key role in the metastatic progression of breast cancer, and as such, their very presence and, in particular, their number in a given volume of patient blood could provide a means for determining patient prognosis and for monitoring the progression of disease. Clinical studies have shown that breast-cancer patients with >5 CTCs in 7.5 mL of whole blood prior to the start of therapy had a shorter progression-free survival and poor overall survival than those with fewer to no CTCs in the same volume of blood. While the clinical and prognostic significance of CTCs continue to be established for metastatic breast cancer, very little is known about CTCs, themselves. Their isolation and classification are extremely difficult because they are extremely rare: 1-10 cells/7.5 mL of peripheral blood.

SUMMARY

Devices for separating constituents (e.g., cells) in a fluid sample are provided. The device includes a microfluidic conduit configured to carry a flow of a fluid sample and includes two or more separation elements, each separation element including a first region and a second region, where the first region has a cross-sectional area less than a cross-sectional area of the second region. The device also includes a flow resistive element in fluid communication with the microfluidic conduit in a region between two adjacent separation elements. Also provided are methods of using the devices, as well as systems and kits that include the devices. The devices, systems, methods and kits find use in a variety of different applications, including diagnostic assays.

Aspects of the present disclosure include a device for separating constituents in a fluid sample. The device includes a microfluidic conduit configured to carry a flow of a fluid sample and having two or more separation elements, where each separation element includes a first region and a second region, and the first region has a cross-sectional area less than a cross-sectional area of the second region. The device also includes a flow resistive element in fluid communication with the microfluidic conduit in a region between two adjacent separation elements.

In some embodiments, the first region and the second region of each separation element are arranged symmetrically about a longitudinal axis of the microfluidic conduit.

In some embodiments, the first region and the second region of each separation element are arranged asymmetrically about a longitudinal axis of the microfluidic conduit.

In some embodiments, the two or more separation elements are arranged in series.

In some embodiments, the two or more separation elements are arranged in parallel.

In some embodiments, the two or more separation elements are arranged in series and in parallel.

In some embodiments, the device includes a first separation element, where the first region and the second region of the first separation element are arranged asymmetrically about a longitudinal axis of the microfluidic conduit, and a second separation element arranged in series with the first separation element, where the first region and the second region of the second separation element are arranged asymmetrically about a longitudinal axis of the microfluidic conduit, and where the flow resistive element is in fluid communication with the microfluidic conduit in a region between the first and second separation elements.

In some embodiments, the device includes a first separation element, where the first region and the second region of the first separation element are arranged symmetrically about a longitudinal axis of the microfluidic conduit, a second separation element arranged in series with the first separation element, where the first region and the second region of the second separation element are arranged asymmetrically about a longitudinal axis of the microfluidic conduit, and a third separation element arranged in series with the first separation element and in parallel with the second separation element, where the first region and the second region of the third separation element are arranged asymmetrically about a longitudinal axis of the microfluidic conduit, and where the flow resistive element is in fluid communication with the microfluidic conduit in a region between the first separation element and the second and third separation elements.

In some embodiments, the flow resistive element includes an elongated conduit with a cross-sectional area less than the cross-sectional area of the second region. In some embodiments, the flow resistive element includes an elongated serpentine conduit.

In some embodiments, the device includes a specific binding region in fluid communication with a downstream end of the microfluidic conduit. In some embodiments, the specific binding region includes a surface having a specific binding member in contact with the flow of the fluid sample. In some embodiments, the specific binding member is an antibody. In some embodiments, the antibody specifically binds to leukocytes.

In some embodiments, the first region has a cross-sectional area ranging from 25 μm to 100 μm.

In some embodiments, the second region has a cross-sectional area ranging from 250 μm to 500 μm.

In some embodiments, the device includes an inlet in fluid communication with an upstream end of the microfluidic conduit.

In some embodiments, the device includes an outlet in fluid communication with a downstream end of the microfluidic conduit.

Aspects of the present disclosure include a system for separating constituents in a fluid sample. The system includes a device and a pressure source. The device includes a microfluidic conduit configured to carry a flow of a fluid sample and having two or more separation elements, where each separation element includes a first region and a second region, and where the first region has a cross-sectional area less than a cross-sectional area of the second region. The device also includes a flow resistive element in fluid communication with the microfluidic conduit in a region between two adjacent separation elements.

In some embodiments, the pressure source includes a fluid pump.

In some embodiments, the system includes a detector. In some embodiments, the detector is a fluorescence detector, a camera, a complementary metal-oxide semiconductor (CMOS), a charge-coupled device (CCD), an intensified charge-coupled device (ICCD), a Coulter counter, or a node-pore sensing device.

Aspects of the present disclosure include a method of separating constituents in a fluid sample. The method includes passing a fluid sample having a plurality of constituents through a device to separate a population of constituents from the constituents in the fluid sample. The device includes a microfluidic conduit having two or more separation elements, where each separation element includes a first region and a second region, and where the first region has a cross-sectional area less than a cross-sectional area of the second region. The device also includes a flow resistive element in fluid communication with the microfluidic conduit in a region between two adjacent separation elements.

In some embodiments, the method includes collecting the population of constituents from an outlet in fluid communication with a downstream end of the microfluidic conduit.

In some embodiments, the population of constituents has an average diameter greater than the average diameter of the constituents in the fluid sample.

In some embodiments, the population of constituents has an average diameter less than the average diameter of the constituents in the fluid sample.

In some embodiments, the fluid sample includes a non-biological sample.

In some embodiments, the fluid sample includes whole blood. In some embodiments, the population of constituents includes circulating tumor cells.

In some embodiments, the method includes characterizing the constituents that pass through the microfluidic conduit.

In some embodiments, passing the fluid sample through the device includes flowing the fluid sample through the microfluidic conduit at a flow rate of 100 µL/min or more.

Aspects of the present disclosure include a kit that includes a device and a packaging configured to contain the device. The device includes a microfluidic conduit having two or more separation elements, where each separation element includes a first region and a second region, and where the first region has a cross-sectional area less than a cross-sectional area of the second region. The device also includes a flow resistive element in fluid communication with the microfluidic conduit in a region between two adjacent separation elements.

In some embodiments, the kit also includes a buffer.

BRIEF DESCRIPTION OF THE FIGURES

FIG. 2 shows a resistive element, A (e.g., element A of the device shown in FIG. 2), used to maintain equal flow at the device's bifurcation. FIG. 2 shows an anti-CD45 antibody reservoir, B (e.g., element B of the device shown in FIG. 2), used to capture white blood cells and further purify the sample.

FIG. 3 (panel A) shows a schematic of a device and its operation. FIG. 3 (panel B) shows time snapshots of a device in operation. Contraction region width was 50 µm and expansion width was 350 µm. Whole blood was injected into the device from the right. WBCs were clearly being separated from the RBCs and platelets. FIG. 3 (panel C) shows a time snapshot of MCF-7-GFP cells flowing into the appropriate device outlet.

Sample flowrate: 200 μl/min Buffer flowrate: 250 μl/min. 800 MCF-7 GFP cells spiked in 1 mL of whole blood.

Figure 40:
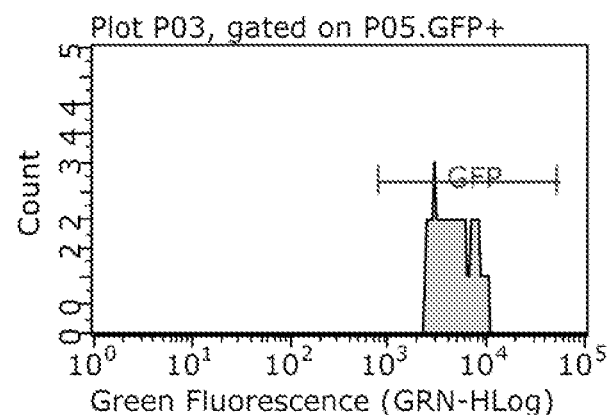

FIG. 40 shows a histogram of GFP Green fluorescence versus Count for device collection. Collection was analyzed with Guava Flow Cytometer. Collection bottom top. Sample flowrate: 200 μl/min Buffer flowrate: 250 μl/min. 800 MCF-7 GFP cells spiked in 1 mL of whole blood.

Figure 41:
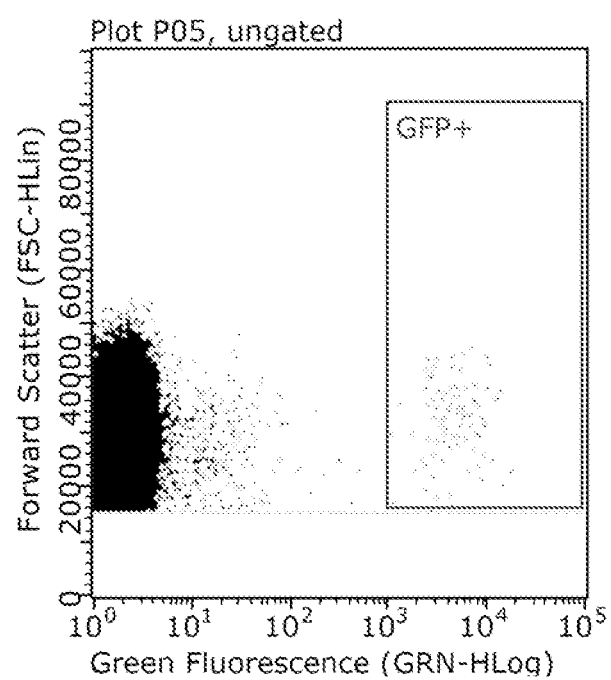

FIG. 41 shows a dot plot of GFP Green fluorescence versus Forward Scatter for device collection. Collection was analyzed with Guava Flow Cytometer. Collection bottom top. Sample flowrate: 200 μl/min Buffer flowrate: 250 μl/min. 800 MCF-7 GFP cells spiked in 1 mL of whole blood.

Figure 42:
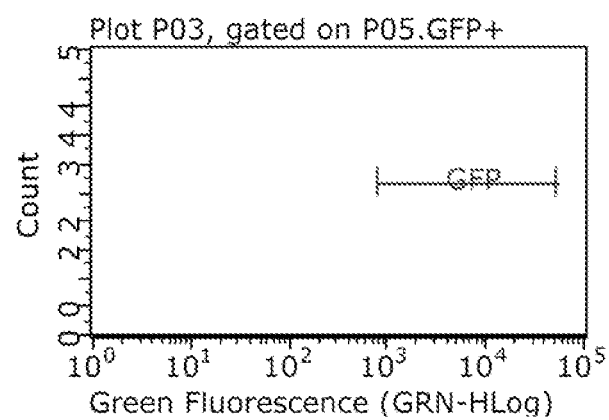

FIG. 42 shoes a histogram of GFP Green fluorescence versus Count for device waste. Waste was analyzed with Guava Flow Cytometer. Waste right top. Sample flowrate: 200 μl/min Buffer flowrate: 250 μl/min. 800 MCF-7 GFP cells spiked in 1 mL of whole blood.

Figure 43:
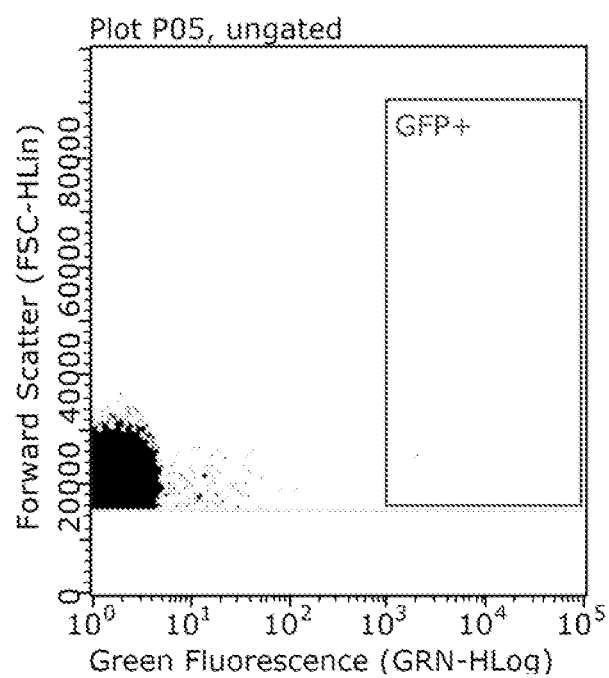

FIG. 43 shows a dot plot of GFP Green fluorescence versus Forward Scatter for device waste. Waste was analyzed with Guava Flow Cytometer. Waste right top. Sample flowrate: 200 μl/min Buffer flowrate: 250 μl/min. 800 MCF-7 GFP cells spiked in 1 mL of whole blood.

DETAILED DESCRIPTION

Devices for separating constituents (e.g., cells) in a fluid sample are provided. The device includes a microfluidic conduit configured to carry a flow of a fluid sample and includes two or more separation elements, each separation element including a first region and a second region, where the first region has a cross-sectional area less than a cross-sectional area of the second region. The device also includes a flow resistive element in fluid communication with the microfluidic conduit in a region between two adjacent separation elements. Also provided are methods of using the devices, as well as systems and kits that include the devices. The devices, systems, methods and kits find use in a variety of different applications, including diagnostic assays.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the present disclosure, embodiments of the devices for separating cells in a fluid sample are described first in greater detail. Following this description, methods of separating cells in a fluid sample, followed by a description of embodiments of systems that include the devices are provided. Finally, a review of the various applications in which the devices, methods, and systems may find use is provided.

Devices

Devices for separating constituents (e.g., cells) in a fluid sample are provided. For example, devices of the present disclosure find use in the separation of cells from each other based on one or more physical characteristics of the cells. In some embodiments, constituents in a fluid sample are separated based on a physical characteristic of the constituents, such as size, shape, mass, or a combination of such physical characteristics. The devices of the present disclosure may also facilitate separation of constituents in a fluid sample based on the fluid dynamics of the constituents as the fluid sample flows through a conduit. For instance, the subject devices may separate constituents in a flow of a fluid through a conduit based on differences in the hydrodynamic properties of the constituents in a fluid sample. In some embodiments, constituents in a fluid sample are separated based on a hydrodynamic property of the constituents, such as lift (e.g., wall lift, shear gradient lift, inertial lift, etc.), drag (e.g., Dean drag), or a combination of such hydrodynamic properties.

During use, a fluid sample may be passed through a conduit of the separation device (e.g., flow through the conduit). In some instances, the fluid sample includes one or more populations of constituents (e.g., cells). For example, the fluid sample may include a first population of constituents (e.g., cells) and a second population of constituents (e.g., cells). The first and second population of constituents may be different from each other based on one or more physical characteristics of the constituents. For instance, cell populations may differ based on average cell size (e.g., average diameter). By "average" is meant the arithmetic mean. As the fluid sample flows through the conduit, constituents in the sample may encounter regions of the conduit with different cross-sectional areas. In some instances, passing the constituents in the sample through the regions of the conduit with different cross-sectional areas causes constituents with different physical characteristics (e.g., different average sizes) and/or different hydrodynamic properties to separate into different flow paths within the conduit. For example, a first population of constituents (e.g., cells with a larger average cell size) may be retained in a first fluid flow path while constituents in a second population, where the physical characteristic of the second population is different from the first population (e.g., smaller average cell size as compared to the first population of cells) may be retained within a second fluid flow path within the conduit. The first and second fluid flow paths, which each contain a different population of constituents as described above, may then be separated from each other, such as by flowing into two different outlets from the conduit, thus separating the different populations of constituents from each other.

Conduits

Accordingly, in certain embodiments, devices of the present disclosure include a conduit configured to carry a flow of a fluid sample. Embodiments of the conduit, as well as other aspects of the devices are described in more detail below.

In certain embodiments, the conduit is sized to accommodate a flow of a fluid sample, where the fluid sample includes constituents, such as cells. The conduit may be sized to have dimensions in the mm and/or μm scale. In some instances, the conduit is a microfluidic conduit, such that the conduit has dimensions (e.g., height and/or width and/or diameter) on the micrometer scale. For example, the conduit may have dimensions (e.g., height and/or width and/or diameter) of 5000 μm or less, 4000 μm or less, 3000 μm or less, 2000 μm or less, 1000 μm or less, 750 μm or less, 500 μm or less, 250 μm or less, 100 μm or less, 75 μm or less, 50 μm or less, 25 μm or less, or 10 μm or less.

As described above, the conduit may be configured to separate constituents in a fluid sample. As such, the conduit may include a separation element. The separation element may facilitate the separation of the constituents in the fluid sample into distinct populations of constituents having different physical properties and/or different hydrodynamic properties. The separation element may include regions having different cross-sectional areas. For example, the separation element may include a first region with a cross-sectional area that is different that the cross-sectional area of a second region of the separation element. In some cases, the separation element includes a first region with a cross-sectional area that is less that the cross-sectional area of a second region of the separation element. In other cases, the separation element includes a first region with a cross-sectional area that is greater that the cross-sectional area of a second region of the separation element. Devices of the present disclosure are also referred to herein as contraction-expansion array (CEA) devices.

Each separation element in the conduit may include at least two regions having different cross-sectional areas. In some cases, a separation element includes more than two such regions. For example, a separation element in the conduit may include a plurality of regions having different cross-sectional areas arranged in series. The separation elements may be arranged in series and may also be adjacent to each other. As described above, a separation element can include a first region having a different cross-sectional area than a second region of the separation element. As such, a separation element in the conduit may have an arrangement of separation regions where the cross-sectional areas of the conduit alternate from smaller to larger to smaller to larger, etc. In other instances, a separation element in the conduit may have an arrangement of separation regions where the cross-sectional areas of the conduit alternate from larger to smaller to larger to smaller, and so forth. In certain embodiments, a separation element includes 2 or more separation regions, such as 4 or more, 6 or more, 8 or more, 10 or more, 12 or more, 14 or more, 16 or more, 18 or more, 20 or more, etc. separation regions.

The conduit may include one separation element, or a plurality of separation elements. In some cases, the conduit includes two or more separation elements. In certain embodiments, the conduit includes 3 or more separation elements, such as 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more separation elements. Conduits of the present disclosure may even include larger numbers of separation elements, such as, but not limited to, 25 or more separation elements, 30 or more, 40 or more, 50 or more, 60 or more, 70 or more, 80 or more, 90 or more, or 100 or more separation elements.

In certain embodiments, the conduit has dimensions (e.g., width and/or diameter) in the range of 0.1 μm to 5000 μm, such as 1 μm to 2500 μm, including 10 μm to 1000 μm in the region of the conduit with the larger cross-sectional area. For example, the conduit may have dimensions in the range of 250 μm to 5000 μm, or 250 μm to 4500 μm, or 250 μm to 4000 μm, or 250 μm to 3500 μm, or 250 μm to 3000 μm, or 250 μm to 2500 μm, or 250 μm to 2000 μm, or 250 μm to 1750 μm, or 250 μm to 1500 μm, or 250 μm to 1250 μm, or 250 μm to 1000 μm, or 250 μm to 750 μm, or 250 μm to 500 μm in the region of the conduit with the larger cross-sectional area. In certain embodiments, the conduit has dimensions (e.g., width) of 350 μm in the region of the conduit with the larger cross-sectional area. Dimensions of the conduit described above also apply to the dimensions of the separation element of the conduit in the region of the separation element having the larger cross-sectional area.

In certain embodiments, the conduit has dimensions (e.g., width and/or diameter) in the range of 0.1 μm to 2500 μm, such as 1 μm to 1000 μm, or 25 μm to 500 μm in the region of the conduit with the smaller cross-sectional area. For example, the conduit may have dimensions (e.g., width) of 1 μm to 2500 μm, such as 1 μm to 2000 μm, or 1 μm to 1750 μm, or 1 μm to 1500 μm, or 1 μm to 1250 μm, or 1 μm to 1000 μm, or 1 μm to 750 μm, or 1 μm to 500 μm, or 5 μm to 250 μm, or 10 μm to 250 μm, or 25 μm to 250 μm, or 25 μm to 100 μm in the region of the conduit with the smaller cross-sectional area. In certain embodiments, the conduit has dimensions (e.g., width) of 50 μm in the region of the conduit with the smaller cross-sectional area. In certain embodiments, the conduit has dimensions (e.g., width) of 60 μm in the region of the conduit with the smaller cross-sectional area. Dimensions of the conduit described above also apply to the dimensions of the separation element of the conduit in the region of the separation element having the smaller cross-sectional area.

In some cases, the ratio of the dimension (e.g., width) of the conduit in the region with the smaller cross-sectional area to the dimension (e.g., width) of the conduit in the region with the larger cross-sectional area is 0.9, such as 0.8, or 0.7, or 0.6, or 0.5, or 0.4, or 0.3, or 0.2, or 0.1. For example, the ratio of the dimension (e.g., width) of the conduit in the region with the smaller cross-sectional area to the dimension (e.g., width) of the conduit in the region with the larger cross-sectional area may be 0.5. In some instances, the ratio of the dimension (e.g., width) of the conduit in the region with the smaller cross-sectional area to the dimension (e.g., width) of the conduit in the region with the larger cross-sectional area is 0.1.

In certain embodiments, the conduit has dimensions (e.g., height and/or diameter) in the range of 0.1 µm to 5000 µm, such as 1 µm to 2500 µm, including 10 µm to 1000 µm in the region of the conduit with the larger cross-sectional area. For example, the conduit may have dimensions in the range of 10 µm to 5000 µm, or 10 µm to 4500 µm, or 10 µm to 4000 µm, or 10 µm to 3500 µm, or 10 µm to 3000 µm, or 10 µm to 2500 µm, or 10 µm to 2000 µm, or 10 µm to 1750 µm, or 10 µm to 1500 µm, or 10 µm to 1250 µm, or 10 µm to 1000 µm, or 10 µm to 750 µm, or 10 µm to 500 µm, or 10 µm to 250 µm, or 10 µm to 200 µm, or 10 µm to 150 µm, or 10 µm or 100 µm, or 25 µm to 100 µm in the region of the conduit with the larger cross-sectional area. In certain embodiments, the conduit has dimensions (e.g., height) of 65-80 µm in the region of the conduit with the larger cross-sectional area. In certain embodiments, the conduit has dimensions (e.g., height) of 75 µm in the region of the conduit with the larger cross-sectional area. Dimensions of the conduit described above also apply to the dimensions of the separation element of the conduit in the region of the separation element having the larger cross-sectional area.

In certain embodiments, the conduit has dimensions (e.g., height and/or diameter) in the range of 0.1 µm to 5000 µm, such as 1 µm to 2500 µm, including 10 µm to 1000 µm in the region of the conduit with the smaller cross-sectional area. For example, the conduit may have dimensions in the range of 10 µm to 5000 µm, or 10 µm to 4500 µm, or 10 µm to 4000 µm, or 10 µm to 3500 µm, or 10 µm to 3000 µm, or 10 µm to 2500 µm, or 10 µm to 2000 µm, or 10 µm to 1750 µm, or 10 µm to 1500 µm, or 10 µm to 1250 µm, or 10 µm to 1000 µm, or 10 µm to 750 µm, or 10 µm to 500 µm, or 10 µm to 250 µm, or 10 µm to 200 µm, or 10 µm to 150 µm, or 10 µm or 100 µm, or 25 µm to 100 µm in the region of the conduit with the smaller cross-sectional area. In certain embodiments, the conduit has dimensions (e.g., height) of 65-80 µm in the region of the conduit with the smaller cross-sectional area. In certain embodiments, the conduit has dimensions (e.g., height) of 75 µm in the region of the conduit with the smaller cross-sectional area. Dimensions of the conduit described above also apply to the dimensions of the separation element of the conduit in the region of the separation element having the smaller cross-sectional area.

In certain embodiments, a separation element of the conduit has a length in the range of 0.1 µm to 2500 µm, such as 1 µm to 1000 µm, or 25 µm to 500 µm. For example, the separation element of the conduit may have a length of 1 µm to 2500 µm, such as 1 µm to 2000 µm, or 1 µm to 1750 µm, or 1 µm to 1500 µm, or 1 µm to 1250 µm, or 1 µm to 1000 µm, or 1 µm to 750 µm, or 1 µm to 500 µm, or 5 µm to 250 µm, or 10 µm to 250 µm, or 25 µm to 250 µm, or 25 µm to 100 µm. In certain embodiments, the separation element of the conduit has a length of 50 µm.

Although in some cases the dimensions of the conduit are described in terms of diameter for conduits having a circular cross-sectional profile, the dimensions described herein also apply to non-circular (e.g., square or rectangular) conduits, such as the width and/or height of a conduit having a non-circular (e.g., square or rectangular) cross-sectional profile.

In some cases, the conduit has a cross-sectional area of 10 mm$^2$ or less, such as 9 mm$^2$ or less, or 8 mm$^2$ or less, or 7 mm$^2$ or less, or 6 mm$^2$ or less, or 5 mm$^2$ or less, or 4 mm$^2$ or less, or 3 mm$^2$ or less, or 2 mm$^2$ or less, or 1 mm$^2$ or less, or 0.75 mm$^2$ or less, or 0.5 mm$^2$ or less, or 0.25 mm$^2$ or less, or 0.1 mm$^2$ or less. For instance, the conduit may have a cross-sectional area of 0.25 mm$^2$ or less. The length of the conduit will generally be greater than its diameter (e.g., the conduit is an elongated conduit). In some instances, the length of the conduit is 1 to 1000 mm, or 1 to 750 mm, or 1 to 500 mm, or 1 to 250 mm, 1 to 100 mm, 1 to 50 mm, such as from 1 to 25 mm, or from 1 to 10 mm, or from 1 to 5 mm. In certain instances, the ratio of the length of the conduit to the diameter is 1000:1, such as 750:1, including 500:1, or 250:1, or 100:1, or 75:1, or 50:1, or 25:1 or 10:1.

Although the dimensions of the conduit have been described above, the dimensions of conduit may vary as desired, and may depend on factors, such as the size and/or shape of the constituents (e.g., cells) to be separated, the fluid, the flow velocity, combinations of these factors, and the like. The cross-sectional profile of the conduit may be circular, square or rectangular. In certain embodiments, the cross-sectional profile of the conduit is rectangular. However, for some applications, it may be desired to use other conduit shapes.

In certain embodiments, the regions within a separation element having different cross-sectional areas are oriented in the x-y plane of the device. For instance, the region within a separation element with the smaller cross-sectional area may be viewed as a section of the conduit having an obstruction or protrusion extending from a side wall of the conduit into the interior of the conduit. The protrusion extends into the interior of the conduit, thus making the interior cross-sectional area of the conduit small in the region containing the protrusion as compared to the interior cross-sectional area of the conduit without a protrusion. The protrusion may be oriented such that it is in the x-y plane of the device, e.g., coplanar with the conduit. In some cases, the protrusion may be oriented such that it extends in a z-direction relative to the plane of the device, e.g., extends up from the bottom of the conduit or extends down from the top of the conduit. Combinations of protrusions in the x-y plane and in the z-direction may be used.

The protrusion may have a shape when viewed from above of that of a square or a rectangle. Other shapes are also possible, such as triangular, trapezoid, or semi-circular shapes (when viewed from above). In some embodiments, the protrusion extends into the interior of the conduit by 1 µm to 1000 µm, or 1 µm to 750 µm, or 1 µm to 500 µm, or 5 µm to 250 µm, or 10 µm to 250 µm, or 10 µm to 250 µm, or 10 µm to 100 µm, or 10 µm to 75 µm, or 10 µm to 50 µm, or 10 µm to 25 µm. In certain cases, the protrusion has a height that is the same as the height of the conduit, such that the flow of the fluid flows around the side of the protrusion and not above or below the protrusion. In some instances, the protrusion has a length of 1 µm to 1000 µm, or 1 µm to 750 µm, or 1 µm to 500 µm, or 5 µm to 250 µm, or 10 µm to 250 µm, or 10 µm to 250 µm, or 10 µm to 100 µm, or 10 µm to 75 µm, or 10 µm to 50 µm, or 10 µm to 25 µm. In certain embodiments, the protrusion has a length of 25 µm.

In some cases, the region within a separation element having the smaller cross-sectional area may have one protrusion, e.g., extending from a side wall of the conduit into the interior of the conduit. As such, this type of separation element may be regarded as an asymmetric separation element. An asymmetric separation element has a first region and a second region having different cross-sectional areas, where the first and second regions are arranged asymmetrically about a longitudinal axis of the conduit. For instance, in a conduit having an asymmetrical separation element, a central longitudinal axis (e.g., a longitudinal axis parallel to and passing through the center of the conduit, such as parallel to and passing through the center of the region of the conduit having the larger cross-sectional area) will not pass through the center of the conduit in the region having the smaller cross-sectional area. Stated another way, in a conduit having an asymmetrical separation element, the region of the separation element having the larger cross-sectional area and the region of the separation element having the smaller cross-sectional area do not share a common central longitudinal axis.

In certain embodiments, an asymmetrical separation element has a first region and a second region having different cross-sectional areas, where the first region has a smaller cross-sectional area than the cross-sectional area of the second region. In other embodiments, an asymmetrical separation element has a first region and a second region having different cross-sectional areas, where the first region has a larger cross-sectional area than the cross-sectional area of the second region.

In other embodiments, the region within a separation element having the smaller cross-sectional area may have a combination of protrusions. For instance, the region within a separation element having the smaller cross-sectional area may have two protrusions, such as a first protrusion extending from a side wall of the conduit into the interior of the conduit and a second protrusion extending from an opposing side wall of the conduit into the interior of the conduit. In some cases, the two opposing protrusions are the same size and shape. As such, this type of separation element may be regarded as a symmetric separation element. A symmetric separation element has a first region and a second region having different cross-sectional areas, where the first and second regions are arranged symmetrically about a longitudinal axis of the conduit. For instance, in a conduit having a symmetric separation element, a central longitudinal axis (e.g., a longitudinal axis parallel to and passing through the center of the conduit, such as parallel to and passing through the center of the region of the conduit having the larger cross-sectional area) will also pass through the center of the conduit in the region having the smaller cross-sectional area. Stated another way, in a conduit having a symmetric separation element, the region of the separation element having the larger cross-sectional area and the region of the separation element having the smaller cross-sectional area share a common central longitudinal axis.

In certain embodiments, a symmetric separation element has a first region and a second region having different cross-sectional areas, where the first region has a larger cross-sectional area than the cross-sectional area of the second region. In other embodiments, a symmetric separation element has a first region and a second region having different cross-sectional areas, where the first region has a smaller cross-sectional area than the cross-sectional area of the second region.

In certain embodiments, the conduit includes a flow resistive element. In some cases, the flow resistive element is in fluid communication with a junction in the conduit, such as in a region of the conduit where the flow of the fluid in the conduit is divided into two or more subsequent conduits. The flow resistive element may provide resistance to the flow of the fluid in the conduit. In some instances, providing resistance to the flow of fluid in the conduit facilitates maintaining a balanced and equal flow through the conduit at a junction in the conduit. The flow resistive element may be configured as an elongated flow resistive conduit having a cross-sectional area less than the cross-sectional area of the region of the conduit with the larger cross-sectional area. In some instances, the flow resistive element includes an elongated serpentine conduit. By elongated is meant that the length of the flow resistive conduit is greater than its diameter. In some instances, the length of the flow resistive conduit is 1 to 1000 mm, or 1 to 750 mm, or 1 to 500 mm, or 1 to 250 mm, 1 to 100 mm, 1 to 50 mm, such as from 1 to 25 mm, or from 1 to 10 mm, or from 1 to 5 mm. In certain instances, the ratio of the length of the flow resistive conduit to the diameter is 1000:1, such as 750:1, including 500:1, or 250:1, or 100:1, or 75:1, or 50:1, or 25:1 or 10:1. In some instances, the flow resistive element is serpentine. By serpentine is meant that the conduit of the flow resistive element is non-linear. For instance, the flow resistive conduit may have one or more bends in the conduit such that a fluid flowing through the flow resistive element has a flow path that changes directions as the fluid flows through the flow resistive element.

In certain embodiments, the conduit includes a first fluid flow path. In some instances, the conduit includes a second flow path. As described above, constituents in a fluid sample may be separated from each other. As such, a first population of constituents may be separated into a first fluid flow path in the conduit, while a second population of constituents is separated into the second fluid flow path in the conduit. The first and second fluid flow paths, each containing different populations of constituents, may be flowed into different outlets from the conduit, thus allowing for individual collection and/or subsequent analysis of the different populations of constituents. For example, the conduit may include a first outlet in fluid communication with a downstream end of the first fluid flow path (e.g., the fluid flow path associated with the first population of separated cells) and may include a second outlet in fluid communication with a downstream end of the second fluid flow path (e.g., the fluid flow path associated with the second population of separated cells). As such, constituents (e.g., cells) of a first population that are retained in the first fluid flow path may be collected at the first outlet, and constituents (e.g., cells) of a second population that are retained in the second fluid flow path may be collected at the second outlet separately from the first population of constituents.

In some cases, the device includes a fluid inlet in fluid communication with an upstream end of the conduit. In some embodiments, the fluid inlet provides an inlet through which a fluid sample may be introduced into the conduit (e.g., a fluid sample containing constituents, such as cells, to be separated). The device may include a first fluid outlet in fluid communication with a downstream end of the conduit. By "upstream" is meant at a position nearer to the source of the fluid flow. By "downstream" is meant at a position further away from the source of the fluid flow. In some embodiments, the device includes a second fluid outlet in fluid communication with a downstream end of the conduit. One of the fluid outlets may be in fluid communication with a flow resistive element as described herein. One of the fluid outlets may be in fluid communication with a fluid inlet of a second device as described herein. As such, multiple devices may be arranged in fluid communication with each other, such as two or more devices arranged in series.

A device as described herein may include a third fluid outlet in fluid communication with a downstream end of the conduit. For example, one fluid outlet may be in fluid communication with a flow resistive element, and the other two fluid outlets may each be in fluid communication with a device as described herein. As such, multiple devices may be arranged in series and in parallel.

In some cases, the device includes a second fluid inlet in fluid communication with an upstream end of the conduit. The second fluid inlet may provide an inlet through which a focusing fluid may be introduced into the conduit. In some cases, the focusing fluid includes a flow of a fluid configured to direct the flow of the sample fluid towards a region within the conduit. For example, the focusing fluid may direct the flow of the sample fluid towards a side wall within the conduit. In some cases, the focusing fluid facilitates separation of the different populations of the cells in the sample as the sample passes through the regions of the conduit with different cross-sectional areas.

In certain embodiments, the conduit is formed in a substrate. For instance, the conduit may be formed as a channel in the substrate. Suitable substrate materials are generally selected based upon their compatibility with the conditions present in the particular operation to be performed by the device. Such conditions can include various pH, temperature, ionic concentration, and solvent tolerance. In certain instances, the substrate material is inert to components of a separation to be carried out by the device. For example, the substrate material may be selected such that the substrate material does not substantially react with the reagents, fluids and/or particles in the samples to be analyzed by the device. Suitable substrate materials include, but are not limited to, glass, quartz, ceramics, and silicon, semiconductor (InAs, GaAs, and the like), as well as polymeric substances, e.g., plastics, such as, but not limited to, polydimethylsiloxane (PDMS), thermoset polyester (TPE), Norland Optical Adhesive (NOA; e.g., NOA 81), and the like. NOA 81 is a mercapto-ester polymer. In some instances, NOA is polymerized by exposure to light, such as UV light (e.g., UV light with a wavelength from 320 nm to 380 nm, such as 365 nm).

In embodiments that include polymeric substrates, the substrate materials may be rigid, semi-rigid, or non-rigid, opaque, semi-opaque, or transparent, depending upon the use for which they are intended. For example, devices which include an optical or visual detection element may be used with substrates that include optically transparent materials to facilitate the optical or visual detection. Alternatively, optically transparent windows of glass or quartz, e.g., may be incorporated into the substrate for these types of detection. As used herein, "optically transparent" means that the material allows light of wavelengths ranging from 180 to 1500 nm, such as from 220 to 800 nm, including from 250 to 800 nm, to be transmitted through the material with low transmission losses. Such light transmissive polymeric materials may be characterized by low crystallinity and include, but are not limited to, polycarbonate, polyethylene terepthalate, polystyrene, polymethylpentene, fluorocarbon copolymers, polyacrylates (including polymethacrylates, such as polymethylmethacrylate (PMMA)), and the like. The polymeric materials may have linear or branched backbones, and may be crosslinked or non-crosslinked. Examples of polymeric materials include, e.g., polydimethylsiloxane (PDMS), polyurethane, polyvinylchloride (PVC), polystyrene, polysulfone, polycarbonate, polymethylmethacrylate (PMMA) and the like. In certain embodiments, the substrate includes polydimethylsiloxane (PDMS).

The substrate may additionally be provided with access ports and/or reservoirs for introducing the various fluid elements needed for a particular analysis, as well as outlets for eliminating the various fluids, as described herein.

In certain embodiments, the conduit is formed in the substrate. For example, the substrate may be configured with a conduit passing through the substrate, or a portion of the substrate (e.g., through a central portion of the substrate). In some instances, the conduit may be formed by removing a portion of the substrate, such as by drilling, boring, punching, coring, etching (e.g., reactive-ion etching, deep reactive-ion etching, chemical etching, wet chemical etching, etc.), and the like. In other instances, the substrate may be formed using a mold that upon removal of the mold leaves a conduit formed through the substrate (or a portion of the substrate as described above). In certain instances, where the conduit is formed in the substrate itself, a cover (as described in more detail below) may not be needed. In some instances, the substrate may be formed using 3D printing methods.

In certain embodiments, the device may be fabricated using printing methods. For instance, the device may be printed using a printer (e.g., a thermal printer, and the like). In some cases, the substrate of the device may be fabricated using printing methods. In certain embodiments, the device may be fabricated using injection molding methods. For instance, the device may be fabricated using an injection mold. In some cases, the substrate of the device may be fabricated using injection molding methods.

In certain embodiments, the device includes a specific binding region in fluid communication with a downstream end of the conduit. In some embodiments, the specific binding region includes a surface having a specific binding member in contact with the flow of the fluid sample. The specific binding member may be attached to the surface of the conduit in the specific binding region of the conduit. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the specific binding member is an antibody. Specific binding of the antibody to its complementary antigen may retain the antigen in the specific binding region of the conduit, thus separating the antigen from the separated cells in the sample. In certain embodiments, the specific binding member is an antibody. For example, the antibody may be an antibody that specifically binds to leukocytes, such as an anti-CD45 antibody.

As described above, devices of the present disclosure include a conduit having two or more separation elements. In some embodiments, the two or more separation elements are arranged in series. In other cases, the two or more separation elements are arranged in parallel. In yet other embodiments, the two or more separation elements are arranged in series and in parallel.

For example, a device of the present disclosure may include a first separation element and a second separation element arranged in series; e.g., the second separation element may be in fluid communication with an outlet from the first separation element. In addition, the device may include a third separation element arranged in series with the first separation element and in parallel with the second separation element; e.g., the third separation element may be in fluid communication with a second outlet from the first separation element. The separation elements in the device may be asymmetrical, symmetric, or a combination of both.

Figure 2:
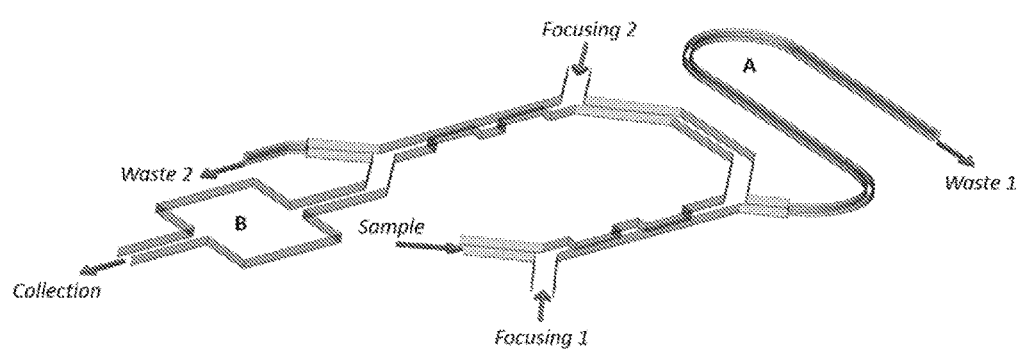
FIG. 2 shows two devices combined in series for sized based cell sorting, according to embodiments of the present disclosure. A sample, such as whole blood, was focused with two focusing fluids and further purified through CD45 negative selection.

Other examples of possible arrangements of separation elements in a device are described below. For instance, in some embodiments, a device includes a first separation element, where the first region and the second region of the first separation element are arranged asymmetrically about a longitudinal axis of the conduit (e.g., a microfluidic conduit). The device may also include a second separation element arranged in series with the first separation element, where the first region and the second region of the second separation element are arranged asymmetrically about a longitudinal axis of the conduit (e.g., the microfluidic conduit). In addition, the device may also include a flow resistive element that is in fluid communication with the conduit in a region between the first and second separation elements. An embodiment of the above described device is shown in FIG. 2.

Figure 18:
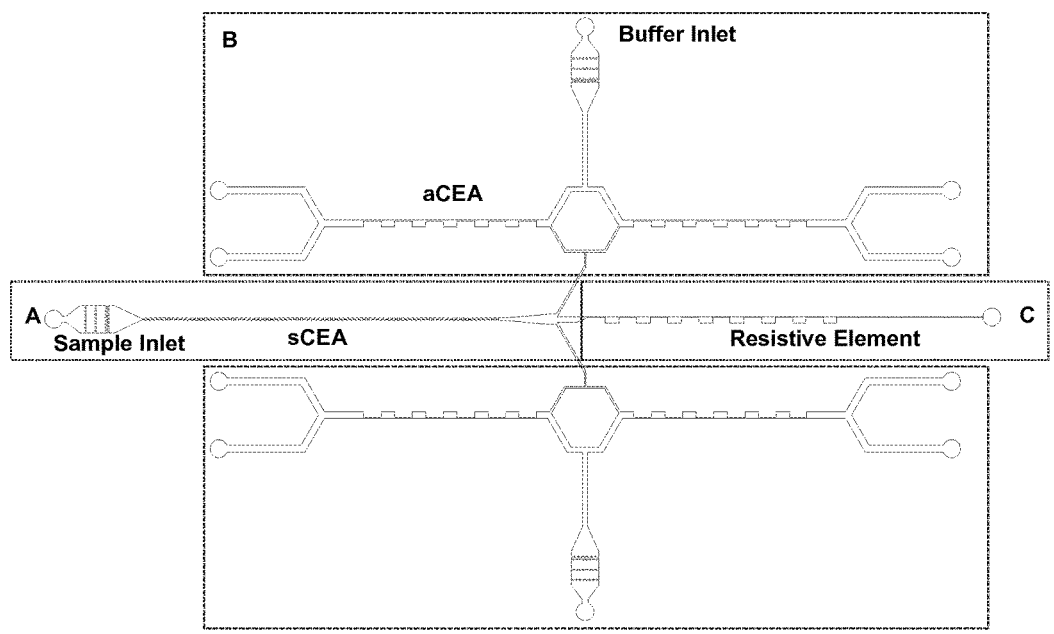
FIG. 18 shows a schematic of an expanded Multistage Separator device, according to embodiments of the present disclosure. Element A of the device is Stage 1, which includes a single sCEA device. This step functions to focus cells to the outer wall through a balance of shear-gradient and wall lift forces. Stage 1 also functions to enrich the concentration of cells in the respective outlet fluid streams. Element B of the device is Stage 2, which includes 4 aCEA devices in parallel. A buffer flow is used to further focus the sample and produce a significant velocity differential within the contraction regions of Stage 2. Element C of the device is a resistive element that balances the flow between Stage 1 and Stage 2. This segment facilitates proportional flows when Stage 1 ends and splits into three channels.

Other examples of arrangements of separation elements in a device are also possible. For example, a device of the present disclosure may include a first separation element, where the first region and the second region of the first separation element are arranged symmetrically about a longitudinal axis of the conduit (e.g., a microfluidic conduit). The device may also include a second separation element arranged in series with the first separation element, where the first region and the second region of the second separation element are arranged asymmetrically about a longitudinal axis of the conduit (e.g., the microfluidic conduit). In some cases, the device also includes a third separation element arranged in series with the first separation element and in parallel with the second separation element, where the first region and the second region of the third separation element are arranged asymmetrically about a longitudinal axis of the microfluidic conduit. The device may also include a flow resistive element that is in fluid communication with the conduit in a region between the first separation element and the second and third separation elements. An embodiment of the above described device is shown in FIG. 18.

Cover

In certain embodiments, the device includes a cover that overlays the substrate to enclose and fluidically seal channels in the substrate to form the conduit. The cover may also include access ports and/or reservoirs for introducing the various fluids and samples needed for a particular analysis, as well as outlets as described herein.

The cover may be attached to the substrate by a variety of means, including, e.g., thermal bonding, adhesives, or in the case of certain substrates, e.g., quartz, glass, or polymeric substrates, a natural adhesion between the two components. In some instances, the cover includes an elastomeric material. For example, an elastomeric cover may form a reversible hermetic seal with a smooth planar substrate. Forming a seal in this manner between the substrate and the cover may facilitate removal of the cover from the substrate such that the substrate and the cover may be washed and re-used. Alternatively, the cover may be bonded to the substrate, forming a permanent bond. Forming a permanent bond between the substrate and the cover may facilitate sealing of the cover to the substrate when higher fluid pressures are used. Bonding methods may be used to secure the cover to the substrate, including activating the elastomer surface, for example by plasma exposure, so that the elastomeric cover will bond when placed in contact with the substrate. In certain cases, the cover and substrate are oxidized in a (DC- or AC-generated) oxygen plasma to increase the hydrophilicity of the conduit and to strengthen the seal to the substrate. Other bonding methods may also be used, such as, but not limited to, adhesives (e.g., light-activated adhesive, such as UV-activated adhesive), mechanical clamping, and the like.

The cover may be made from an elastomer, such as, but not limited to, polyisoprene, polybutadiene, polychloroprene, polyisobutylene, poly(styrene-butadiene-styrene), polyurethane, and silicone. Polymers incorporating materials such as chlorosilanes or methyl-, ethyl-, and phenylsilanes, and polydimethylsiloxane (PDMS), or aliphatic urethane diacrylates may also be used. In some cases, the cover is made from materials, such as polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(l-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), and elastomeric compositions of polyvinylchloride (PVC), polysulfone, polycarbonate, polymethylmethacrylate (PMMA), and polytertrafluoroethylene (Teflon).

In certain embodiments, the thickness of the cover ranges from 0.1 μm to 10 cm, such as from 1 μm to 5 cm, including from 10 μm to 2 cm, or from 100 μm to 10 mm. In some cases, the cover has a thickness of 1 mm to 5 mm, such as 3 mm thick.

Reservoirs

In certain embodiments, the device includes one or more reservoirs, such as one or more fluid reservoirs. The reservoirs may be configured to contain a fluid and/or direct the fluid to or from the conduit. For example, the device may include two reservoirs, such as a first reservoir and a second reservoir. The first reservoir may be in fluid communication with an end of the conduit, such as the upstream end of the conduit. The first reservoir may be configured to contain a fluid (e.g., a sample fluid), and direct the fluid to the upstream end of the conduit. The second reservoir may be in fluid communication with the other end of the conduit, such as the downstream end of the conduit. The second reservoir may be configured to contain the fluid exiting the downstream end of the conduit, such as for collection of a population of separated constituents. Additional reservoirs may be provided, for instance in embodiments with two or more fluid outlets at the downstream end of the conduit, individual reservoirs may be provided at each of the separate fluid outlets.

In certain embodiments, the conduit is formed in the substrate as described above. For instance, the conduit may be formed as a channel in the substrate. Applying the cover to the substrate, as described above, may result in the formation of an enclosed conduit. Similarly, applying the cover to the substrate may result in two or more enclosed reservoirs in fluid communication with the conduit. Each of the reservoirs may be adapted to contain a fluid, such as a fluid sample that includes one or more constituents (e.g., cells). In certain cases, the reservoirs are configured to contain a fluid volume of 1 μL or more, such as 5 μL or more, including 10 μL or more, or 25 μL or more, or 50 μL or more, or 75 μL or more, or 100 μL or more, or 250 μL or more, or 500 μL or more, or 750 μL or more, or 1 mL or more.

In certain cases, the reservoir includes an inlet port. A fluid sample may be introduced into the reservoir through the inlet port. In certain instances, the reservoir includes an outlet port. A fluid can be transferred from the reservoir through the outlet port. A wide range of suitable sizes of inlets and outlets are possible, and those of skill in the art are capable of empirically determining the desired size ranges depending upon the nature of the fluid or the cells to be analyzed. In some cases, the reservoir includes a filter. For example, the reservoir positioned upstream from the conduit may include a filter configured to prevent large particles from clogging the conduit. In other cases, the device does not include a filter. For example, the size of the conduit may be large enough such that the risk of clogging is relatively low.

In certain embodiments, the subject devices and systems include one or more of the devices and/or systems described in U.S. Pat. No. 7,279,883, PCT/US2012/059088, filed Feb. 20, 2014 (published as WO 2013/052890), and PCT/US2014/024574, filed Mar. 15, 2014, the disclosures of each of which are incorporated herein by reference.

Systems

Aspects of the present disclosure include a system for separating cells in a fluid sample. The system includes a device for separating cells in a fluid sample, as described herein. As described above, the device includes a conduit (e.g., a microfluidic conduit) configured to carry a flow of a fluid sample, where the conduit includes two or more separation elements, each separation element having a first region and a second region, where the first region has a cross-sectional area less than a cross-sectional area of the second region. As described herein, the device also includes a flow resistive element in fluid communication with the conduit in a region between two adjacent separation elements.

In certain embodiments, the system includes one or more devices as described herein, such as 2 or more devices, e.g., 3 or more, 4 or more, 5 or more, 10 or more, 20 or more, 30 or more, 40 or more, 50 or more, 60 or more, 70 or more, 80 or more, 90 or more, 100 or more, etc. The devices may be arranged in the system in series and/or in parallel. For example, the system may include two or more devices arranged in series. In some cases, the system includes two or more devices arranged in parallel. In some cases, the system includes several devices arranged in series and in parallel.

FIG. 18 shows a multistage CEA separation device: Element A of the device is Stage 1, which includes an sCEA device. This stage functions to focus constituents in a sample (e.g., cells) to the outer wall through a balance of shear-gradient and wall lift forces. Stage 1 also functions to enrich the fluid. Element B of the device is Stage 2, which includes four aCEA devices arranged in parallel to each other and which is arranged in series with respect to Stage 1. A buffer flow is used to further focus the sample and produce a significant velocity differential within the contraction regions of Stage 2 (i.e., the regions having the smaller cross-sectional area). Element C of the device is a resistive element that balances the flow between Stage 1 and Stage 2. This segment provides for proportional flow when Stage 1 ends and splits into three channels.

The systems of the present disclosure may further include a fluid delivery system, such as a microfluidic or nanofluidic fluid delivery system. Microfluidic fluid delivery systems may include systems where the total volume of biological solution at any one time is 1000 microliters or less. Nanofluidic fluid delivery systems may include systems where the total volume of biological solution at any one time is 1000 nanoliters or less. Depending on the requirements of the assay being conducted, fluid delivery systems that are capable of delivering larger volumes of fluid may also be used, e.g., milliliter fluid delivery systems, etc. The fluid deliver system may include one or more pressure sources (e.g., fluid pumps) configured to provide a flow of a fluid through the device.

Aspects of the presently disclosed system also provide for an integrated "chip" having one or more of the subject microfluidic devices for sorting cells. In certain embodiments, the chip includes a plurality of devices, such as 2 or more devices, or 4 or more devices, or 6 or more, or 8 or more, or 10 or more devices. The two or more devices may be arranged in series (e.g., with a first device positioned upstream from a second device) or in parallel (e.g., with a first and second devices arranged in parallel), or a combination thereof, as described herein.

In some embodiments, two or more devices may be provided in a vertical arrangement of devices (e.g., stacked onto another). In the vertical arrangement of devices, the outlet of one device may be in fluid communication with the inlet of the next device, as described herein.

In certain embodiments, upstream from the device may be included one or more of a filtration system, a dilution system, and a system to adjust the driving force of the fluid medium. The system may also include an optical detection device for further analytical applications, such as for multiplexed assays or analysis of heterogeneous mixtures. For example, fluorescence of the various cells may be detected as well as the size and type of cells, as described above.

Detector

In certain embodiments, the system includes a detector. The detector may be configured to detect cells that are passing through or have already passed through the conduit. For example, the detector may be configured to detect a first population of cells flowing through the first fluid flow path of the conduit. In some instances, the detector may be configured to detect a second population of cells flowing through the second flow path of the conduit. In certain embodiments, the detector is configured to quantify the cells. The detector may include a camera, complementary metal-oxide semiconductor (CMOS), charge-coupled device (CCD), intensified charge-coupled device (ICCD), fluorescence detector, combinations thereof, and the like.

In certain embodiments, the detector includes electrodes to perform a Coulter counter or resistive-pulse measurement (e.g., the current changes each time a cell passes through the detector in the microfluidic channel). In some cases, the detector provides for counting of the cells (e.g., quantification of the cells). In certain embodiments, the detector includes a field-effect transistor (FET), mos-FET, and the like.

Methods

Aspects of the present disclosure include a method of separating constituents (e.g., cells) in a fluid sample. The method includes passing a fluid sample that includes a plurality of constituents (e.g., cells) through a microfluidic conduit. Passing the fluid sample through the conduit may include introducing the fluid sample into the conduit, such as, for example introducing the fluid sample into the conduit through an input port or a reservoir in fluid communication with an upstream end of the conduit. The fluid sample may be passed through (e.g., flowed through) the conduit by application of a pressure to the fluid in the conduit, such as by applying a pressure using fluid handling components, such as a fluid pump.

As described above, the conduit includes two or more separation elements, each separation element having a first region and a second region, where the first region has a cross-sectional area less than a cross-sectional area of the second region. As described herein, the device also includes a flow resistive element in fluid communication with the microfluidic conduit in a region between two adjacent separation elements.

Embodiments of the methods are directed to determining whether a population of constituents (e.g., cells) is present in a sample, e.g., determining the presence or absence of one or more populations of constituents (e.g., cells) in a sample. In certain embodiments of the methods, the presence of one or more populations of constituents (e.g., cells) in the sample may be determined qualitatively or quantitatively. Qualitative determination includes determinations in which a simple yes/no result with respect to the presence of a population of constituents (e.g., cells) in the sample is provided to a user. Quantitative determination includes both semi-quantitative determinations in which a rough scale result, e.g., low, medium, high, is provided to a user regarding the amount of constituents (e.g., cells) in the sample, and fine scale results in which an exact measurement of the amount of the cells is provided to the user.

Samples that may be assayed with the subject microfluidic devices may vary, and include both simple and complex samples. Simple samples are samples that include the constituents (e.g., cells) of interest, and may or may not include one or more molecular entities that are not of interest, where the number of these non-interest molecular entities may be low, e.g., 10 or less, 5 or less, etc. Simple samples may include biological or other samples that have been processed in some manner, e.g., to remove potentially interfering molecular entities from the sample. By "complex sample" is meant a sample that may or may not have the constituents (e.g., cells) of interest, but also includes many different proteins, cells and/or other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., size, deformability, shape, etc.).

In certain embodiments, the samples of interest are biological samples, such as, but not limited to, urine, blood (e.g., whole blood), serum, plasma, saliva, semen, prostatic fluid, nipple aspirate fluid, lachrymal fluid, perspiration, feces, cheek swabs, cerebrospinal fluid, amniotic fluid, gastrointestinal fluid, biopsy tissue, cell lysate samples, pleural effusion liquid, and the like. The sample can be a biological sample or can be extracted from a biological sample derived from humans, animals, plants, fungi, yeast, bacteria, tissue cultures, viral cultures, or combinations thereof using conventional methods. In certain embodiments, the sample is a fluid sample, such as a solution of cells in a fluid. The fluid may be an aqueous fluid, such as, but not limited to water, saline, a buffer, and the like.

In certain instances, the sample is a whole blood sample. In some cases, red blood cells (RBCs), platelets, and/or white blood cells (WBCs, also referred to herein as leukocytes) have a smaller average size than the cells of interest (e.g., metastatic cancer cells) and will be separated away from larger sized cells into a distinct fluid flow path (e.g., the second fluid flow path) as described herein. In some instances, different flow paths may be used to remove RBCs, platelets and white blood cells (WBCs) from the fluid flow. In some cases, the RBCs and/or platelets may be lysed before or after isolation. In some cases, the device may be treated with bovine serum albumin (BSA) prior to flowing the sample through the device, which may facilitate a reduction in clogging of the device.

In certain instances, the method includes separating the cells to determine the presence of the cells in the fluid sample. Because separating the cells of interest is based on physical characteristics of the cells, such as average size and/or hydrodynamic properties (rather than, for example fluorescence-based detection techniques), in some embodiments, the cells are not labeled prior to passing the sample through the conduit. In some cases, the method further includes quantifying the number of cells that pass through the conduit. For instance, the number of cells of interest may be counted as the cells of interest flow through the conduit. In some instances, cells not of interest are not significantly included in the quantification of the cells of interest.

In certain embodiments, the method includes characterizing the cells as the cells pass through the conduit. A variety of characteristics about the cells may be characterized by the device. For example, characterizing the cells may include determining the average size of the cells, such as the average diameter of the cells.

In some cases, characterizing the cells includes determining the type of cells that are passing through the conduit. For instance, a physical characteristic of the cells of interest may be determined, such as the size of the cells. In these embodiments, the method may include determining whether a first population of cells is larger (or smaller) than other populations of cells (e.g. a second population of cells).

In certain instances, cells to be separated and characterized are suspended at an appropriate concentration in a suitable liquid medium, e.g., a fluid sample. The fluid sample may include any suitable liquid media (either aqueous or nonaqueous), for example, liquid media such as, but not limited to, water, saline, buffer, organic solvents, cell cultures, animal or human bodily fluids, solutions including particles and/or biological molecules, cellular cytoplasm, cellular extracts, cellular suspensions, solutions of labeled particles or biological molecules, solutions including liposomes, encapsulated material, or micelles, etc. may be used.

A variety of driving mechanisms may be used to produce a flow of the sample fluid through the device. For example, electrophoretic, electrokinetic or electroosmotic forces, or pressure gradients may be used. In some instances, the method includes applying a pressure to the fluid to provide a flow of the fluid through the device. Other embodiments may include pumping the fluid through the device to provide a flow of the fluid through the device. The rate of flow in delivering the fluid sample to the device may be selected to allow sufficient time for the device to sort the cells as they flow through the device. For example, the flow rate may be 0.1 µL/min or more, such as 0.5 µL/min or more, or 1 µL/min or more, or 5 µL/min or more, or 10 µL/min or more, or 25 µL/min or more, or 50 µL/min or more, or 75 µL/min or more, or 100 µL/min or more, or 150 µL/min or more, or 200 µL/min or more. In some instances, the flow rate is 150 µL/min. In some instances, the flow rate is 100 µL/min. In some instances, the flow rate is 200 µL/min. In certain embodiments, the method has a detection sensitivity of detecting 1-10 cells of interest (e.g., circulating tumor cells, CTCs, or circulating endothelial cells, CECs) in 7.5 mL of sample.

In some embodiments, the methods include the uniplex analysis of a population of cells in a sample. By "uniplex analysis" is meant that a sample is analyzed to detect the presence of one population of cells in the sample. For example, a sample may include a mixture of cells of interest and other molecular entities that are not of interest. In some cases, the methods include the uniplex analysis of the sample to determine the presence of the cells of interest in the sample mixture.

Certain embodiments include the multiplex analysis of two or more populations of cells in a sample. By "multiplex analysis" is meant that the presence two or more distinct cells, in which the two or more populations of cells are different from each other, is determined. For example, cells may include differences in physical characteristics, such as size. In some instances, the number of populations of cells is greater than 2, such as 3 or more, 4 or more, 5 or more, etc., up to 10 or more, e.g., 20 or more distinct populations of cells. In certain embodiments, the methods include the multiplex analysis of 2 to 20 distinct populations of cells, such as 2 to 10 distinct cell populations, including 2 to 5 distinct cell populations.

Methods of the present disclosure also include methods of fabricating the devices described herein. The conduit can be formed by a variety of methods. In some embodiments, the conduit is etched into a substrate which is then sealed by a cover (e.g., an elastomeric cover as described herein). In other embodiments, the conduit can be molded into the cover (e.g., the elastomeric cover as described herein) which is then laid on top of the substrate. In other embodiments, the substrate may be formed into the desired shape using a mold. For example, a substrate precursor solution may be placed into a mold. The substrate precursor solution may include substrate precursor compounds that retain a desired shape when exposed to an external stimulus. For instance, the substrate precursor solution may include substrate precursor monomers that polymerize upon exposure to light, such as UV light. The mold may be removed leaving the conduit, which has retained the desired shape and configuration.

Manufacturing of devices may be carried out by any number of microfabrication techniques. For example, lithographic techniques may be employed in fabricating glass, quartz or silicon substrates, for example, with methods known in the semiconductor manufacturing industries. Photolithographic masking, plasma or wet etching and other semiconductor processing technologies may be used to define microscale elements in and on substrate surfaces. Alternatively, micromachining methods, such as laser drilling, micromilling and the like, may be employed. Similarly, for polymeric substrates, manufacturing techniques such as, but not limited to, injection molding techniques or stamp molding methods may be used. In some cases, large numbers of substrates may be produced using, e.g., rolling stamps to produce large sheets of microscale substrates, or polymer microcasting techniques where the substrate is polymerized within a microfabricated mold.

Examples of methods of fabricating the devices and systems of the present disclosure are provided herein. It is to be understood that embodiments of the present disclosure are not limited to fabrication by one or the other of these methods. Rather, other suitable methods of fabricating the present devices, including modifying the present methods, are also contemplated. One method involves a series of lithographic processes in which the reservoirs and conduit are etched into a planar substrate. These methods can be used to make a large number of devices on a single chip, thus increasing efficiency through parallelization. Another method involves producing a conduit and reservoirs in an elastomeric cover which is then contacted with the substrate.

Utility

The subject devices, systems and methods find use in a variety of different applications where determination of the presence or absence, and/or quantification of one or more constituents in a sample is desired. In some cases, the subject devices, systems and methods find use in separating constituents of different sizes in sample from each other.

For example, the subject devices, systems and methods find use in detecting and/or separating constituents in a non-biological sample, such as, but not limited to, colloids, flavoring particles used in food industry, paint nanoparticles, etc.

In certain embodiments, the subject devices, systems and methods find use in detecting and/or separating constituents in a biological sample, such as, but not limited to, detecting and/or separating different cell populations in a sample. In certain embodiments, the methods are directed to the detection of cells in a sample. For example, the methods may be used in the rapid, clinical detection of one or more cells in a biological sample, e.g., as may be employed in the diagnosis of a disease condition in a subject, in the ongoing management or treatment of a disease condition in a subject, etc. In addition, the subject devices, systems and methods may find use in protocols for the detection of cells in a sample for sorting cells of interest from other components of the sample.

The subject device can be used to isolate rare cells, such as circulating tumor cells and other residual disease cells, in peripheral blood. The subject device can also be used to perform CBCs, in combination with one or more of the devices and/or systems described in U.S. Pat. No. 7,279,883, PCT/US2012/059088, filed Feb. 20, 2014 (published as WO 2013/052890), and PCT/US2014/024574, filed Mar. 15, 2014, the disclosures of each of which are incorporated herein by reference.

In certain embodiments, the subject devices, systems and methods find use in detecting cells. In some cases, the subject devices, systems and methods may be used to detect the presence or absence of particular cells, as well as an increase or decrease in the concentration of particular cells in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, amniotic fluid, gastrointestinal fluid, biopsy tissue, cell lysate samples, pleural fluid, and the like. One or more distinct cell populations may be detected. For example, one or more distinct cell populations may be detected, where the cell populations differ from each other by one or more physical characteristic, such as average cell size.

The presence or absence of a type of cell or significant changes in the concentration of a type of cell can be used to diagnose disease risk, presence of disease in an individual, or to tailor treatments for the disease in an individual. For example, the presence of particular cells may influence the choices of drug treatment or administration regimes given to an individual. In evaluating potential drug therapies, the presence and/or amount of a particular cell may be used as a surrogate for a natural endpoint such as survival or irreversible morbidity. If a treatment alters the presence and/or amount of a particular cell, which has a direct connection to improved health, the presence and/or amount of the cells can serve as a surrogate endpoint for evaluating the clinical benefit of a particular treatment or administration regime. Thus, personalized diagnosis and treatment based on the particular cells or panel of cells detected in an individual are facilitated by the subject devices, systems and methods. Furthermore, the early detection of cells associated with diseases is facilitated by the high sensitivity of the subject devices and systems. Due to the capability of detecting multiple cells on a single chip, combined with sensitivity, scalability, and ease of use, the presently disclosed devices, systems and methods finds use in portable and point-of-care or near-patient molecular diagnostics.

In certain embodiments, the subject devices, systems and methods find use in detecting cells for a disease or disease state. In some cases, the disease is a cellular proliferative disease, such as but not limited to, a cancer, a tumor, a papilloma, a sarcoma, or a carcinoma, and the like. For example, the subject devices, systems and methods find use in detecting the presence of a disease, such as a cellular proliferative disease, such as a cancer, tumor, papilloma, sarcoma, carcinoma, or the like. In some instances, the subject devices, systems and methods find use in detecting the presence of one or more populations of cells associated with a disease, such as a cellular proliferative disease, such as a cancer, tumor, papilloma, sarcoma, carcinoma, or the like.

For example, the subject devices, systems and methods may be used to detect and/or quantify leukemia or cancer cells, such as, but not limited to, acute promyelocytic leukemia (APL) cells in a subject. Rapid diagnosis of APL may facilitate earlier administration of treatment protocols to the subject. For example, the subject devices and methods may have an assay time of 15 minutes or less, such as 10 minutes or less, or 7 minutes or less, or 5 minutes or less, or 3 minutes or less, or 2 minutes or less, or 1 minute or less. The subject devices, systems and methods also find use in detecting and/or isolating and/or quantifying cells that indicate minimal residual disease (MRD). In certain embodiments, MRD cells are leukemic cells (e.g., cancer cells from the bone marrow) that remain in a subject during treatment, or after treatment when the subject is in remission (e.g., substantially no symptoms of disease). In some instances, in cancer treatment, such as treatment of leukemia, detecting and/or isolating and/or quantifying MRD cells may facilitate one or more of the following: determining the effectiveness of cancer treatment or whether traces of cancer remain in the subject, comparing the efficacy of different treatments, monitoring patient remission status, detecting recurrence of the leukemia or cancer, and choosing an appropriate treatment for a patient.

The subject devices, systems and methods also find use in isolating and screening circulating tumor cells (CTCs) in a subject. In some instances, quantification of CTC levels in a subject may facilitate evaluation and tracking of metastatic progression in the subject. The subject devices, systems and methods may also be used to screen CTCs for specific surface biomarkers, which may facilitate the characterization of the particular CTCs in the subject.

The subject devices, systems and methods also find use in isolating and screening circulating endothelial cells (CECs) in a subject. In some instances, quantification of CEC levels in a subject may facilitate evaluation and tracking of vascular injury and/or disease in the subject. The subject devices, systems and methods may also be used to screen CECs for specific surface biomarkers, which may facilitate the characterization of the particular CECs in the subject. For example, CECs (e.g., mature CECs) may be shed by injured or diseased blood vessels, endothelial progenitor cells (EPCs), and may be recruited from the bone marrow for repair, localizing at the injured/diseased site to aid in new vessel formation. In some cases, subjects with ischemia, vascular trauma, acute myocardial infarction, sickle-cell anemia, vasculitis, pulmonary hypertension, and deep-vein thrombosis may have higher levels of CECs as compared to healthy controls (who may have virtually no CECs). In some instances, the number of CECs correlates with the severity of injury or disease. Thus, the subject devices, systems and methods find use in detecting and/or isolating and/or quantifying CECs for diagnostic and prognostic assays.

The subject device, systems and methods find use in diagnostic assays, such as, but not limited to, the following: detecting and/or quantifying cells in a sample, as described above; screening assays, where samples are tested at regular intervals for asymptomatic subjects; prognostic assays, where the presence and or quantity of cells of interest are used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the weight and operating cost are less than the typical stationary laboratory equipment. The subject systems and devices may be integrated into a single apparatus, such that all the steps of the assay, including detection and sorting of a particle of interest, may be performed by a single apparatus. In addition, the subject systems and devices can be utilized in a home setting for over-the-counter home testing by a person without medical training to detect one or more particles in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a device as described in detail herein. In some instances, the kit includes a packaging for containing the device. In certain embodiments, the packaging may be a sealed packaging, e.g., in a water vapor-resistant container, optionally under an air-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.). The kits may further include a buffer. For instance, the kit may include a buffer, such as a sample buffer, a wash buffer, and the like. The kits may further include additional reagents, such as but not limited to, detectable labels (e.g., fluorescent labels, colorimetric labels, chemiluminescent labels, multicolor reagents, enzyme-linked reagents, avidin-streptavidin associated detection reagents, radiolabels, gold particles, magnetic labels, etc.), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc.

Another form can be a computer readable medium, e.g., CD, DVD, Blu-Ray, computer-readable memory (e.g., flash memory), etc., on which the information has been recorded or stored. Yet another form that may be present is a website address which may be used via the Internet to access the information at a removed site. Any convenient form of instructions may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Figure 1:
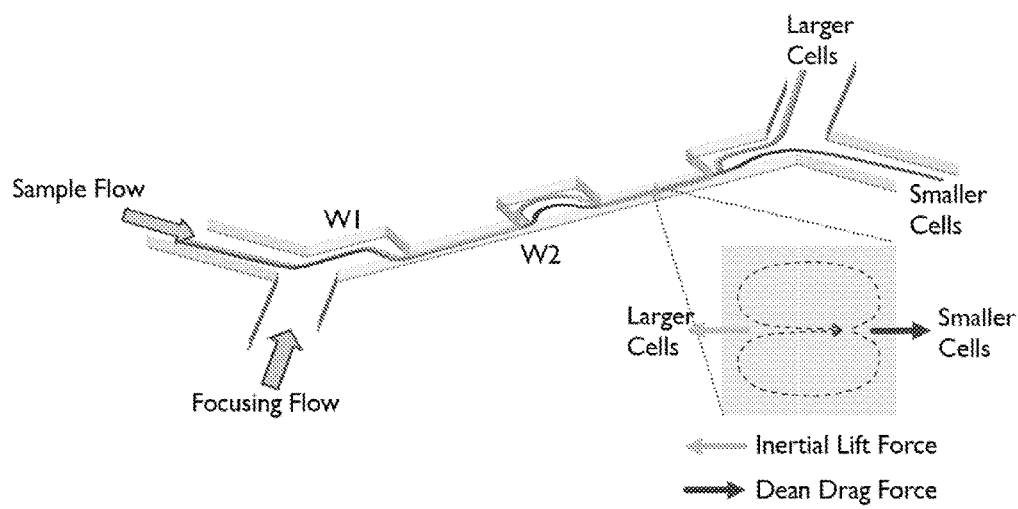
FIG. 1 shows a device for separating cells based on size, according to embodiments of the present disclosure.

A multi-stage device that separated cells by size was produced and tested, for example to isolate rare cells such as circulating tumor cells in peripheral blood. The device included of a series of "contraction-expansion" array (CEA) devices, which utilized a balance of inertial forces (inertial-lift force vs. Dean drag force) to separate cells based on size. As shown in FIG. 1, this device included a single microchannel that had alternating expansion and contraction regions; i.e., alternating regions having a larger cross-sectional area and regions having a smaller cross-sectional area. The changes in the cross sectional area due to the expansion and contraction areas accelerated and decelerated the flow velocity and induced Dean-like flow. When undiluted, whole blood was injected into the CEA device, an inertial-lift force ($F_L = \rho U_m^2 a_p^4 C_L/D_h^2$, where $\rho$, $U_m$, $a_p$, $C_L$, and $D_h$ are the fluid density, x-axial maximum flow velocity, particle diameter, lift coefficient, and hydraulic diameter, respectively) dominated the larger-sized cells, e.g., white blood cells (WBCs, also known as leukocytes), to sidewall W1 and to a specific output. In contrast, a Dean-drag force ($F_D = 3\pi\rho U_{Dean} a_p$, where $U_{Dean}$ is the transverse velocity by Dean flow) dominated and directed smaller-sized cells, e.g., red blood cells (RBCs) and platelets, to the opposite sidewall W2 and to a different output.

Several of the devices were connected in series to improve filtration efficiency, as shown in FIG. 2. When connecting two CEA devices in series, the collection outlet of the first device led to the inlet of a second device and was no longer exposed to atmosphere. To minimize an imbalance in resistance and pressure a resistive element was used to balance flow between the collection and waste outlet of the first CEA, as shown as Element A of the device shown in FIG. 2. In addition, a region directly connected to the output was included that was functionalized with a saturating concentration of anti-CD45 antibodies, as shown as Element B of the device shown in FIG. 2. The antibodies captured the white blood cells only, not cancer or other rare cells, due to specific binding, thus removing the white blood cells from the processed sample. Thus, a high purity sample was obtained. The device was high throughput.

Example 2

Shed from primary solid tumors and having entered into the blood stream, circulating tumor cells (CTCs) may play a role in the metastatic progression of breast, prostate, lung, and colon cancers, etc. Their presence and number in a given volume of patient blood may provide a diagnostic for determining patient prognosis and for monitoring disease progression. Clinical studies have shown that breast-cancer patients with >5 CTCs in 7.5 mL of whole blood before the start of therapy had shorter median progression-free survival and overall survival compared to those with fewer or no CTCs in the same volume of blood. Other clinical studies have shown a correlation between the number of CTCs present prior to therapy and survival in patients with colon or prostate cancer. As such, it may be useful to isolate and classify CTCs, as they are extremely rare: as few as 1-10 cells in 7.5 mL of peripheral blood. Isolating and characterizing these cells may facilitate the identification of appropriate therapy, tracking the progression of disease, and monitoring therapy resistance or decreases in sensitivity.

Typical techniques for isolating and identifying CTCs rely either on the physical properties of these cells (e.g., size, buoyant density, charge, cellular mass, and deformability) or on the expression of particular markers, such as EpCAM, in combination with CK8, 18, and/or 19. Since CTCs are larger than red blood cells (RBCs), isolation based on cell size via membrane filters has been performed. However, such isolation includes contaminating leukocytes (whose size range overlaps with that of CTCs), which then need to be removed from the sample. In addition, CTCs can be subjected to high shear stress when filters are used (especially when the filters become increasingly clogged), leading to potential cell damage.

In contrast to size isolation, the CellSearch system (Veridex) is based on the immunomagnetic separation of fixed EpCAM+ cells from centrifuged blood and subsequent immunostaining of CD45 (to identify contaminating leukocytes), and CK8, 18, and/or 19. However, these types of assays may have low sensitivity.

Other devices may negatively select for CTCs, using: 1) deterministic lateral displacement to remove RBCs and platelets from a blood sample; 2) inertial focusing to align the remaining WBCs and CTCs in a microfluidic channel; and 3) immunomagnetic separation to deplete WBCs tagged with CD45- or CD15-coated magnetic beads. However, contamination with leukocytes that had failed to bind to the magnetic beads is still an issue. In addition, the device does not immediately identify CTC subpopulations. To determine which cells express EpCAM, EMT or stem-cell markers, standard immunostaining is employed. Cells are consequently either fixed or (if live-cell staining is utilized) irreversibly changed by, for example, the undesired initiation of cell signaling, which could then affect molecular characterization.

The device of the present disclosure could be generally applied to other cancers such as colon, prostate, lung, and melanoma. Our method will involve isolating candidate CTCs based on size. The device of the present disclosure includes the label-free capability to isolate and screen CTCs from whole blood. The device of the present disclosure provides both clinicians and researchers a means to enumerate accurately CTCs and their subpopulations from a cancer patient, and identify appropriate therapy, track the progression of disease, and monitor resistance and/or decrease in sensitivity to therapy.

Label-Free Fractionation of Whole Blood

Figure 3:
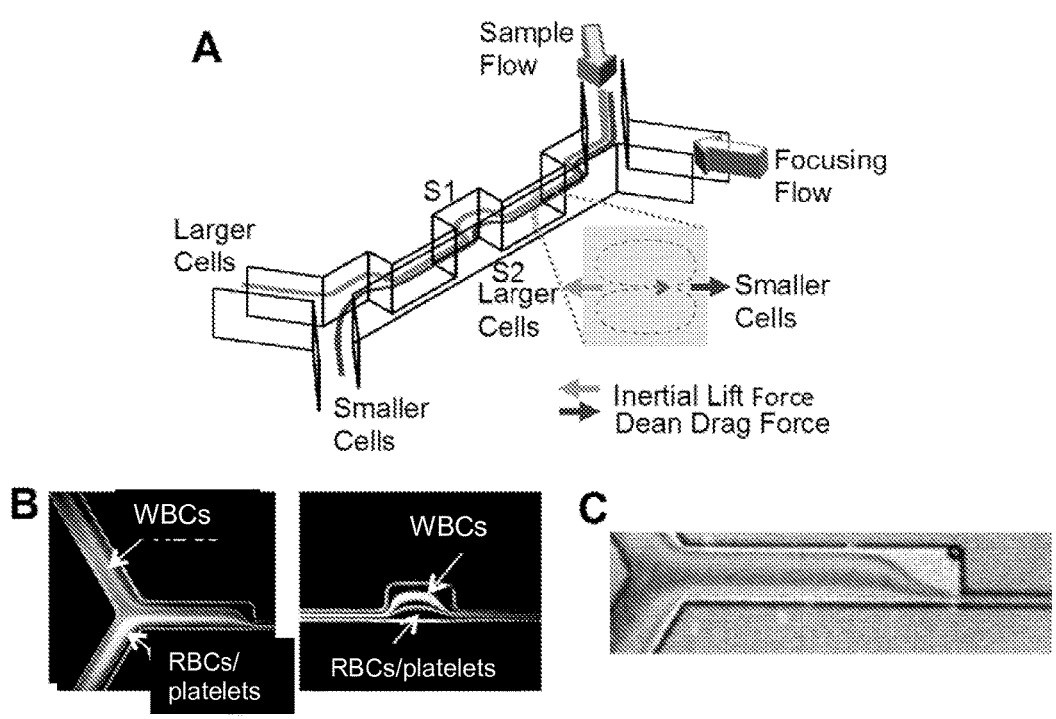
FIG. 3 shows a device according to embodiments of the present disclosure.

The device of the present disclosure included a high-throughput asymmetric "contraction-expansion" array (aCEA) device, which utilized a balance of inertial forces (inertial-lift force vs. Dean drag force) to separate cells based on size. As shown in FIG. 3 (panel A), the device included a single microchannel that had alternating expansion and contraction regions. The changes in the cross sectional area due to the expansion and contraction areas accelerated and decelerated the flow velocity and induced Dean-like flow. When undiluted, whole blood was injected into the aCEA device, an inertial-lift force ($F_L = \rho U_m^2 a_p^4 C_L / D_h^2$, where $\rho$, $U_m$, $a_p$, $C_L$, and $D_h$ are the fluid density, x-axial maximum flow velocity, particle diameter, lift coefficient, and hydraulic diameter, respectively) dominated the larger-sized cells, e.g., white blood cells (WBCs), to sidewall s1 and to a specific output. In contrast, a Dean-drag force ($F_D = 3\pi \rho U_{Dean} a_p$, where $U_{Dean}$ is the transverse velocity by Dean flow) dominated and directed smaller-sized cells, e.g., red blood cells (RBCs) and platelets, to the opposite sidewall s2 and to a different output.

Figure 16:
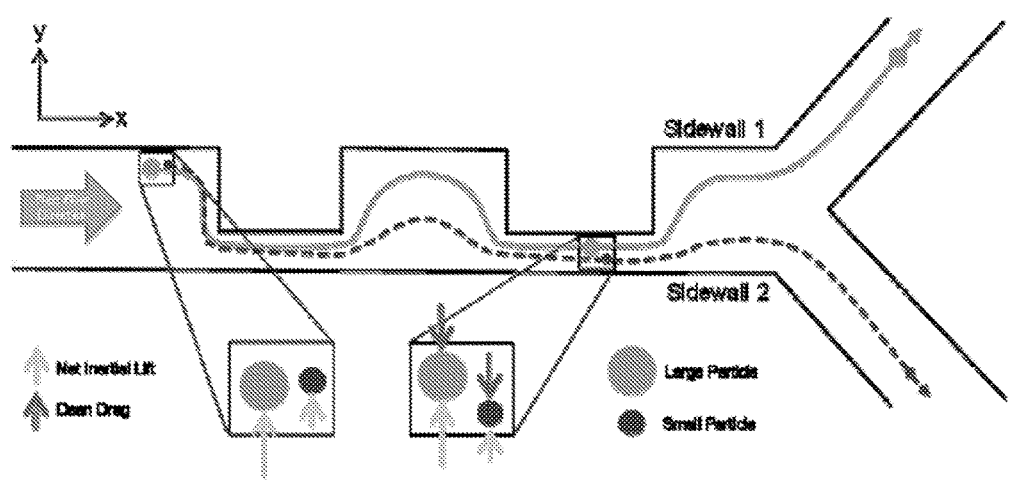
FIG. 16 shows a schematic drawing illustrating Dean drag force focusing of small particles in an asymmetric contraction expansion array (aCEA), according to embodiments of the present disclosure. While inertial lift forces direct larger sized cells toward Sidewall 1, Dean drag forces direct smaller cells toward Sidewall 2. Cells can thus be separated into two different outlets.

FIG. 16 shows a schematic drawing illustrating Dean drag force focusing of small particles in an asymmetric contraction expansion array (aCEA), according to embodiments of the present disclosure. While inertial lift forces direct larger sized cells toward Sidewall 1, Dean drag forces direct smaller cells toward Sidewall 2. Cells can thus be separated into two different outlets.

An asymmetric CEA, aCEA, device was fabricated, which included 6 "contraction-expansion" units (e.g., separation regions having different cross-sectional areas as described herein) into which healthy human donor blood was injected at a flow rate of 150 μL/min (corresponding to a Reynold's number, Re, of 12.6, well below the Re ~30 that damages cells). As shown in FIG. 3 (panel B), as blood passed through the contraction-expansion units, WBCs and RBCs/platelets were continually separated from each other and into different outlets. FIG. 3 (panel C) shows a time snapshot of MCF-7-GFP cells flowing into the appropriate device outlet. Healthy human donor blood spiked with MCF-7 GFP cells (1000:1, WBC: MCF-7 GFP) was also injected into the aCEA device. Coulter counter measurements showed that the waste outlet only had cells that were <12 μm in size; no MCF-7 GFP cells (>15 μm) were present. In contrast, the collection outlet had predominately cells >13 μm in size (e.g., MCF-7 GFP and WBCs). Although the MCF-7-GFP cells were mixed with comparable-sized WBCs in the collection outlet, >95% of the RBCs/platelets in whole blood were successfully removed. A live/dead assay was performed on the collected MCF-7 GFP's and >98% of the cells were viable. In addition, the cells were successfully cultured after collection.

The aCEA device used in this example included a single aCEA device having more than 5 asymmetric contraction-expansion arrays, depending on the desired exposure of cells to Dean drag forces generated in the contraction region (i.e., the separation region having a smaller cross-sectional area). The contraction regions were 50-60 μm in width, 900-1200 μm in length, and 65-80 μm in height. The expansion regions (i.e., the separation region having a larger cross-sectional area) were 350 μm in width, 700-1000 μm in length, and 65-80 μm in height. The ranges in dimensions provided flexibility when targeting different specific cell size thresholds. Data shown in FIGS. 4A to 14B were obtained with the aCEA device described above, which was made out of polydimethylsiloxane (PDMS) and created using soft lithography. The aCEA device, however, could be made out of other different materials as described in the present disclosure.

The aCEA device was validated through isolated experiments. Device function was confirmed with a Millipore Guava Flowcytometer. Whole blood spiked with MCF-7 GFP breast cancer cells was injected into the aCEA device at a chosen rate of 5 μl/min in the sample inlet and phosphate buffered saline (PBS) solution was injected at a chosen rate of 95 μl/min in the buffer inlet. As shown in FIGS. 4A to 14B, MCF-7 GFP cells were found in the collection outlet and none were found in the waste outlet. Data collected from experiments using the above aCEA device is shown in FIGS. 4A to 14B, described below.

Figure 4A:
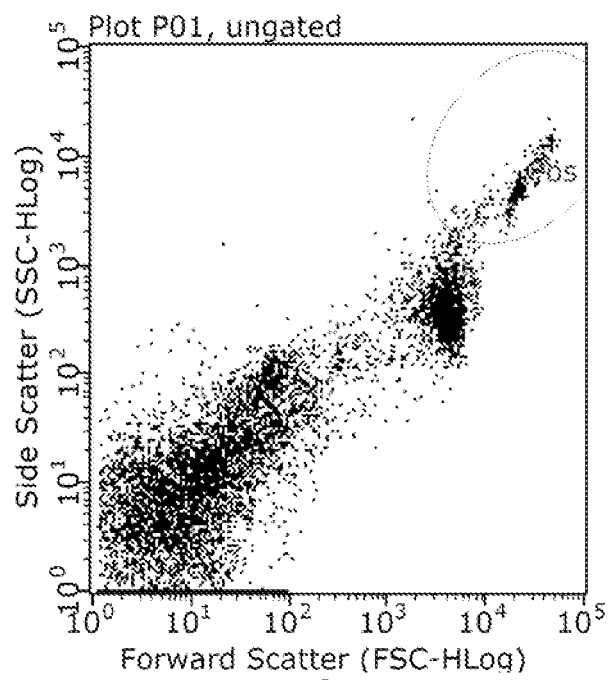
FIG. 4A and FIG. 4B show positive control dot plots (MCF-7 GFP in PBS 1×: Positive control, dot plot) from an experiment where healthy human whole blood was spiked with MCF-7 GFP breast cancer cells at a ratio of 1000:1, MCF-7 GFP to white blood cells (WBC). The blood sample was not diluted. Maximum total flow rate in the device was 116.6 µL/min.
Figure 4B:
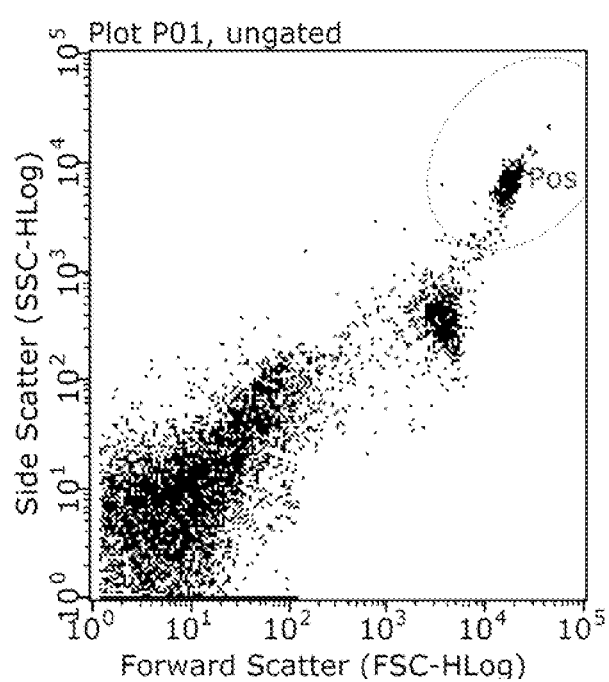

FIG. 4A and FIG. 4B show positive control dot plots (MCF-7 GFP in PBS 1×: Positive control, dot plot) from an experiment where healthy human whole blood was spiked with MCF-7 GFP breast cancer cells at a ratio of 1000:1, MCF-7 GFP to white blood cells (WBC). The blood sample was not diluted. The total flow rate in this device was 100 μL/min.

Figure 5A:
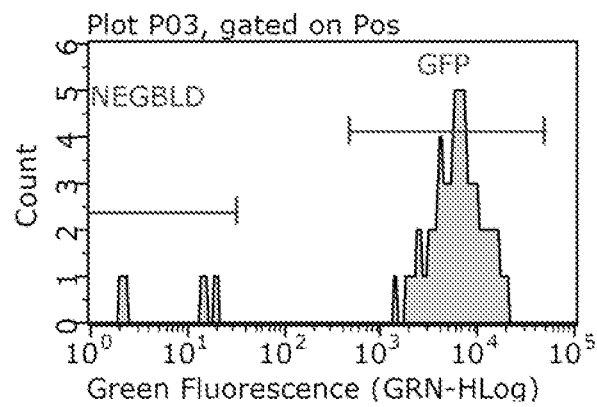
FIG. 5A and FIG. 5B show histograms of GFP Expression gated as high intensity green florescence for the experiment of FIG. 4A and FIG. 4B.
Figure 5B:
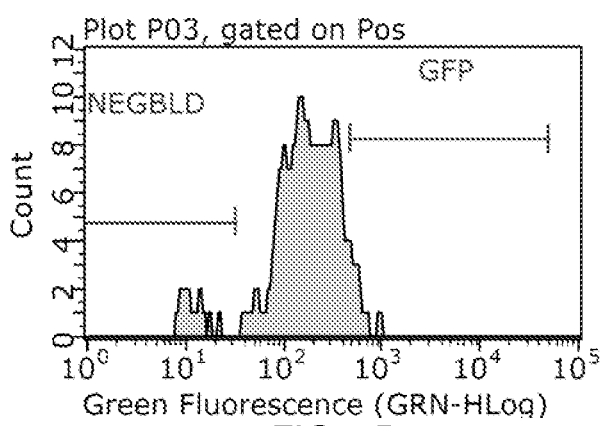

FIG. 5A and FIG. 5B show histograms of GFP Expression gated as high intensity green florescence for the experiment of FIG. 4A and FIG. 4B.

Figure 6A:
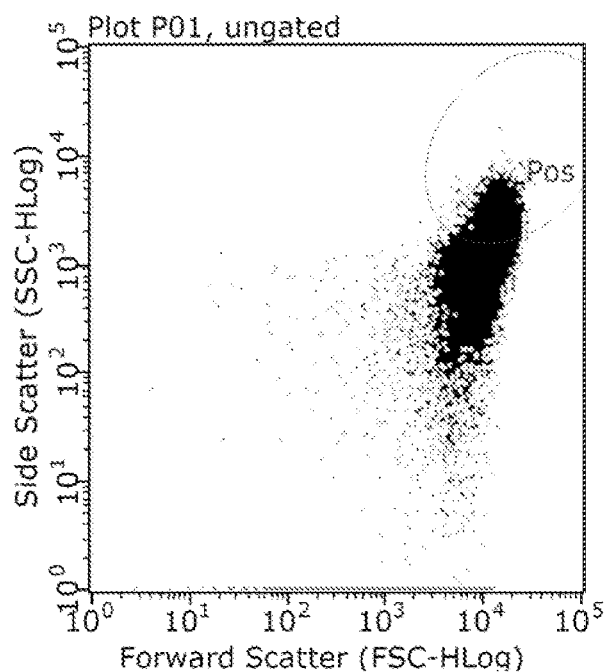
FIG. 6A and FIG. 6B show Collection Outlet dot plots (Positive GFP expression region gated) for the experiment of FIG. 4A and FIG. 4B.
Figure 6B:
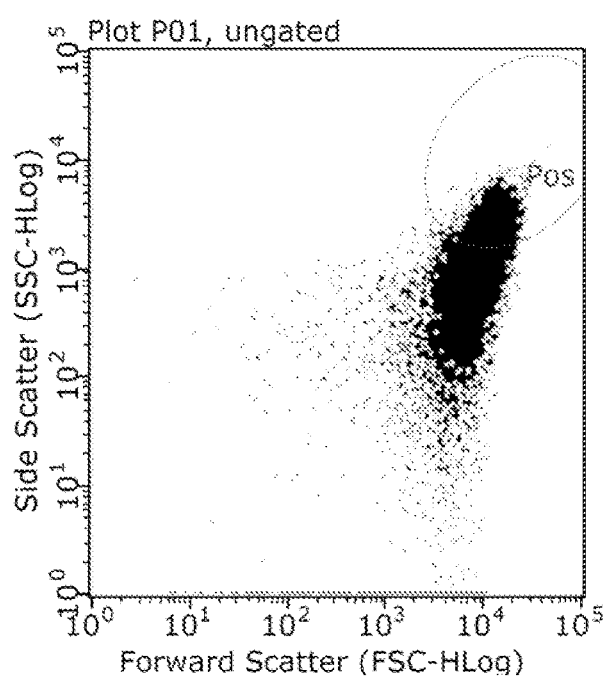

FIG. 6A and FIG. 6B show Collection Outlet dot plots (Positive GFP expression region gated) for the experiment of FIG. 4A and FIG. 4B.

Figure 7A:
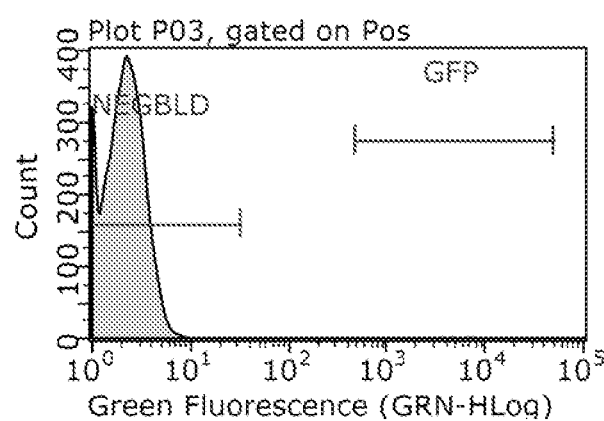
FIG. 7A and FIG. 7B show collection outlet histograms of gated "Pos" region in dot plot (NEGBLD: Negative/Blood Region; GFP: Green Florescence Protein expression region) for the experiment of FIG. 4A and FIG. 4B.
Figure 7B:
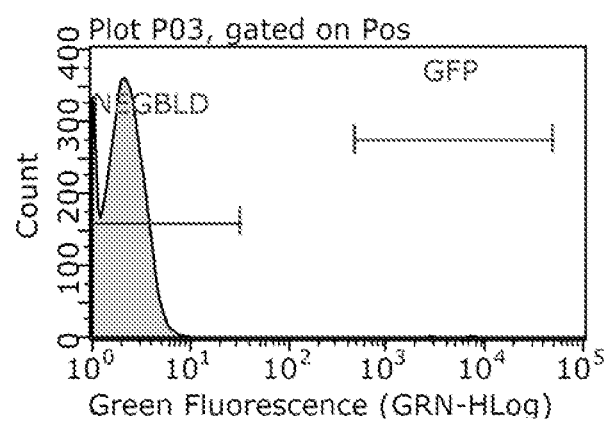

FIG. 7A and FIG. 7B show collection outlet histograms of gated "Pos" region in dot plot (NEGBLD: Negative/Blood Region; GFP: Green Florescence Protein expression region) for the experiment of FIG. 4A and FIG. 4B.

Figure 8A:
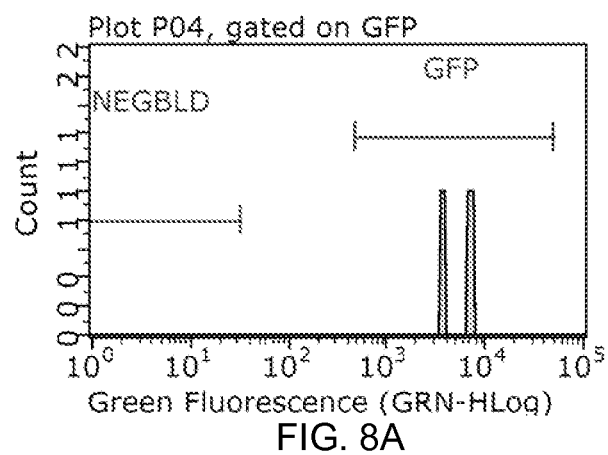
FIG. 8A and FIG. 8B show collection outlet histograms of "GFP" gated region (Captured MCF-7 GFP cells) for the experiment of FIG. 4A and FIG. 4B. This plot scales down to counts of up to 2 cells and neglects negative and blood populations.
Figure 8B:
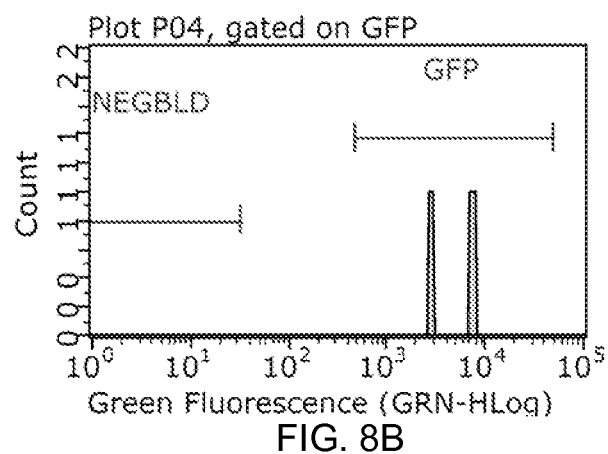

FIG. 8A and FIG. 8B show collection outlet histograms of "GFP" gated region (Captured MCF-7 GFP cells) for the experiment of FIG. 4A and FIG. 4B. This plot scales down to counts of up to 2 cells and neglects negative and blood populations.

Figure 9A:
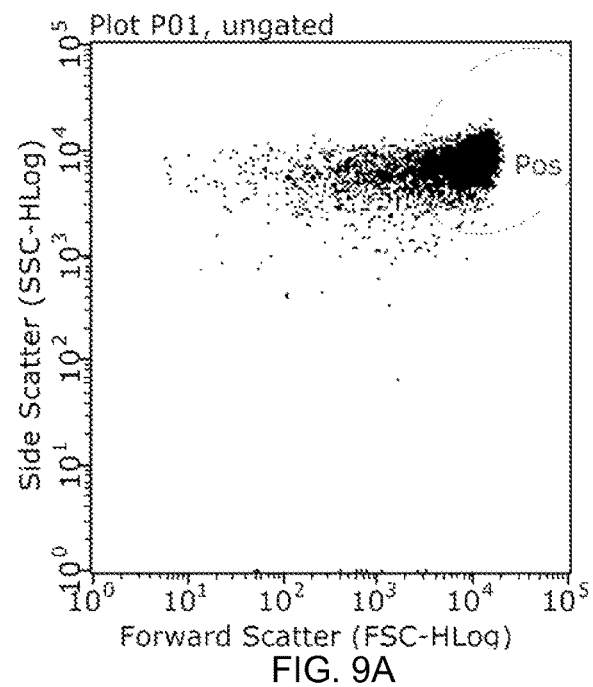
FIG. 9A and FIG. 9B show Waste 1 Outlet dot plots (Positive GFP expression region gated) for the experiment of FIG. 4A and FIG. 4B.
Figure 9B:
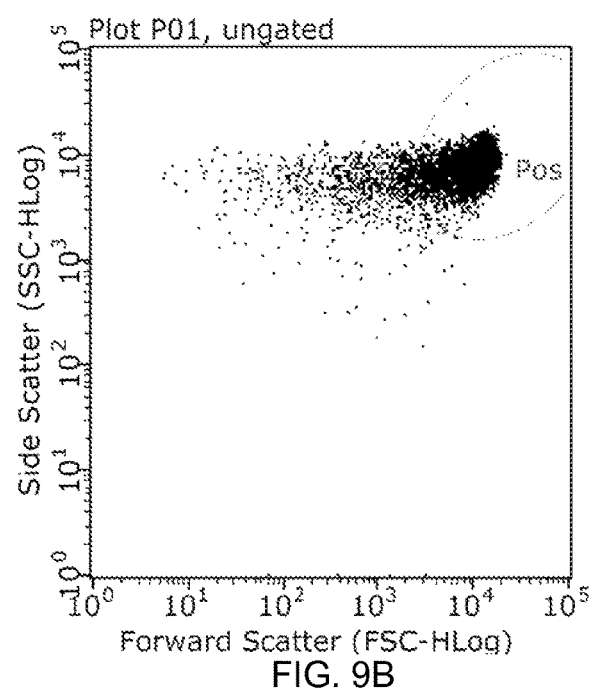

FIG. 9A and FIG. 9B show Waste 1 Outlet dot plots (Positive GFP expression region gated) for the experiment of FIG. 4A and FIG. 4B.

Figure 10A:
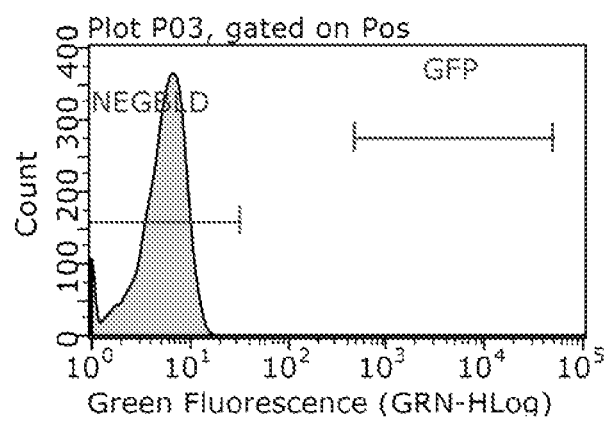
FIG. 10A and FIG. 10B show Waste 1 Outlet histograms of gated "Pos" region in dot plot for the experiment of FIG. 4A and FIG. 4B.
Figure 10B:
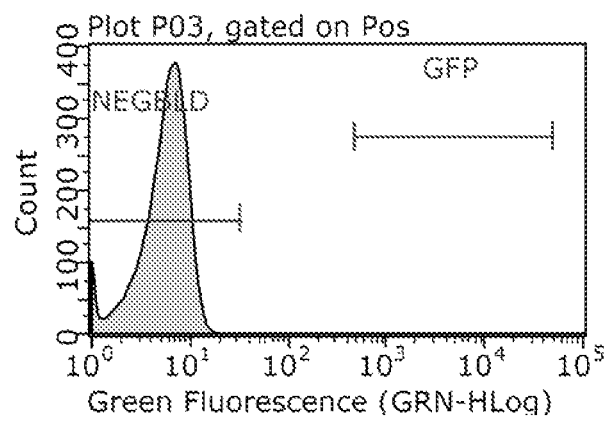

FIG. 10A and FIG. 10B show Waste 1 Outlet histograms of gated "Pos" region in dot plot for the experiment of FIG. 4A and FIG. 4B.

Figure 11A:
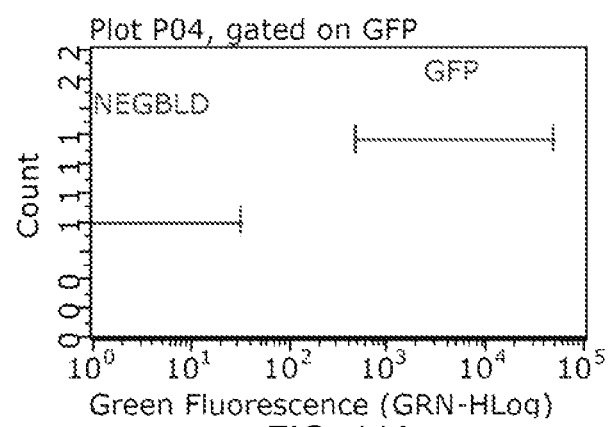
FIG. 11A and FIG. 11B show Waste 1 Outlet histograms of "GFP" gated region. for the experiment of FIG. 4A and FIG. 4B. Zero MCF-7 GFP cells were lost. This plot scales down to counts of up to 2 cells and neglects negative and blood populations.
Figure 11B:
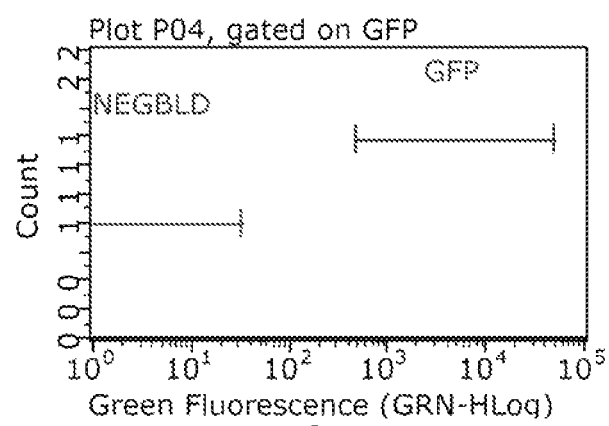

FIG. 11A and FIG. 11B show Waste 1 Outlet histograms of "GFP" gated region. for the experiment of FIG. 4A and FIG. 4B. Zero MCF-7 GFP cells were lost. This plot scales down to counts of up to 2 cells and neglects negative and blood populations.

Figure 12A:
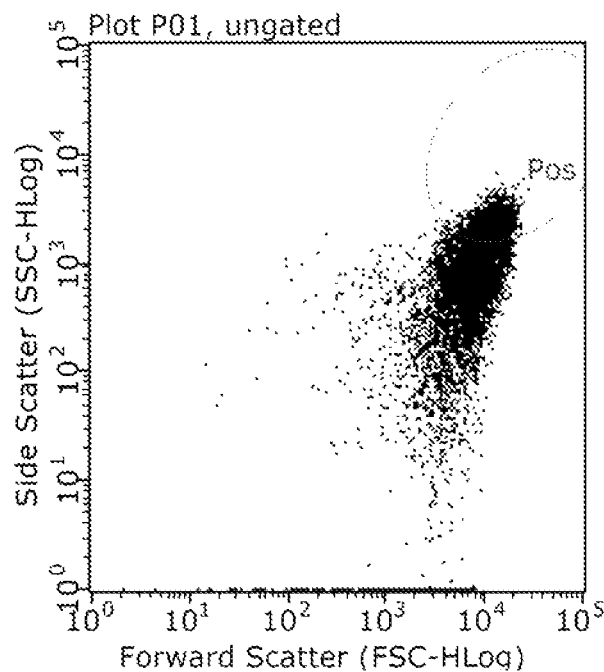
FIG. 12A and FIG. 12B show Waste 2 Outlet dot plot (Positive GFP expression region gated) for the experiment of FIG. 4A and FIG. 4B.
Figure 12B:
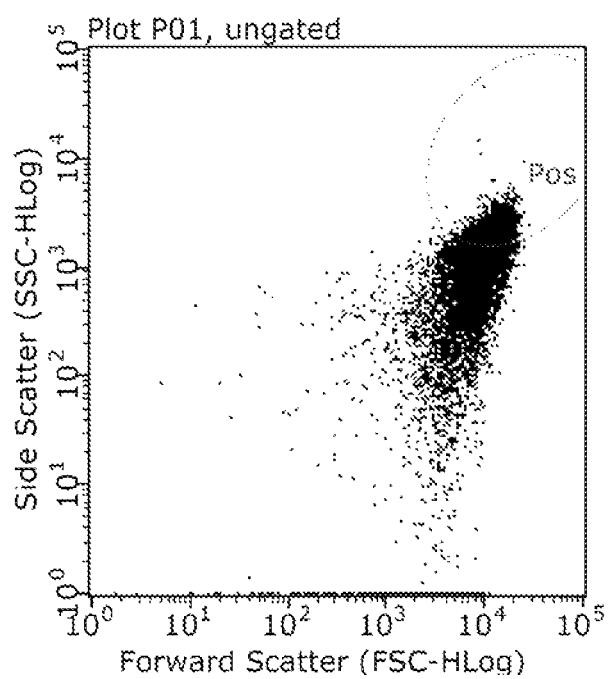

FIG. 12A and FIG. 12B show Waste 2 Outlet dot plot (Positive GFP expression region gated) for the experiment of FIG. 4A and FIG. 4B.

Figure 13A:
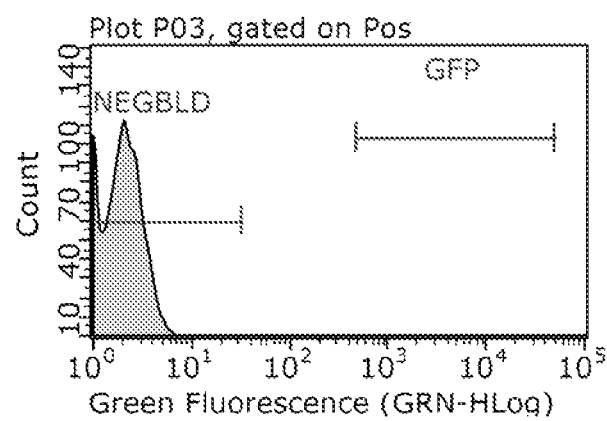
FIG. 13A and FIG. 13B show Waste 2 Outlet histograms of gated "Pos" region in dot plot for the experiment of FIG. 4A and FIG. 4B.
Figure 13B:
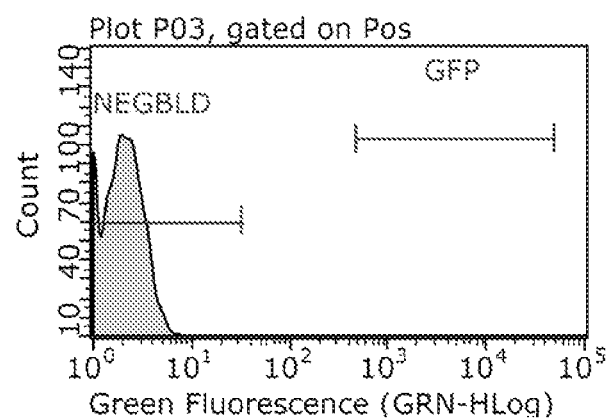

FIG. 13A and FIG. 13B show Waste 2 Outlet histograms of gated "Pos" region in dot plot for the experiment of FIG. 4A and FIG. 4B.

Figure 14A:
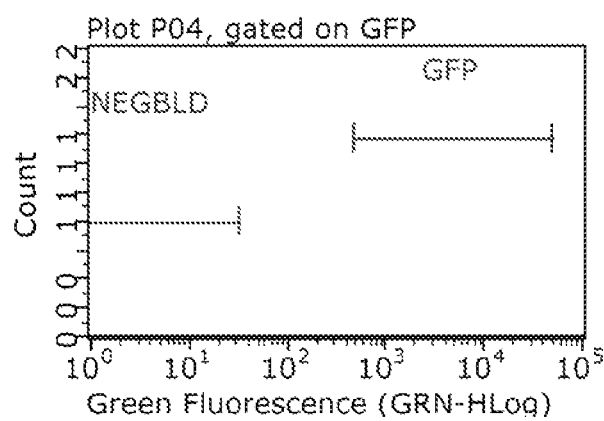
FIG. 14A and FIG. 14B show Waste 2 Outlet histograms of "GFP" gated region (Captured MCF-7 GFP cells) for the experiment of FIG. 4A and FIG. 4B. This plot scales down to counts of up to 2 cells and neglects negative and blood populations.
Figure 14B:
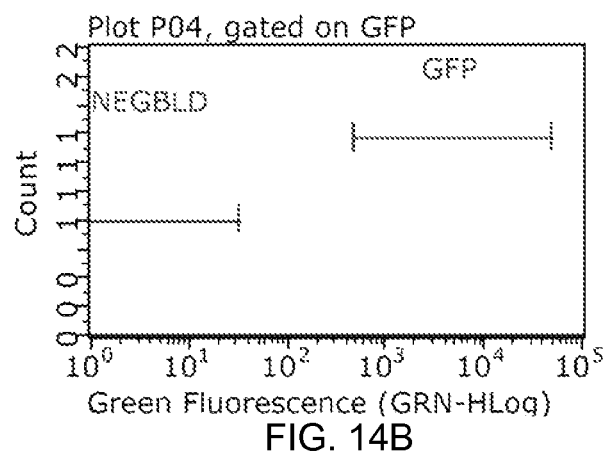

FIG. 14A and FIG. 14B show Waste 2 Outlet histograms of "GFP" gated region (Captured MCF-7 GFP cells) for the experiment of FIG. 4A and FIG. 4B. This plot scales down to counts of up to 2 cells and neglects negative and blood populations.

Example 3

Figure 15:
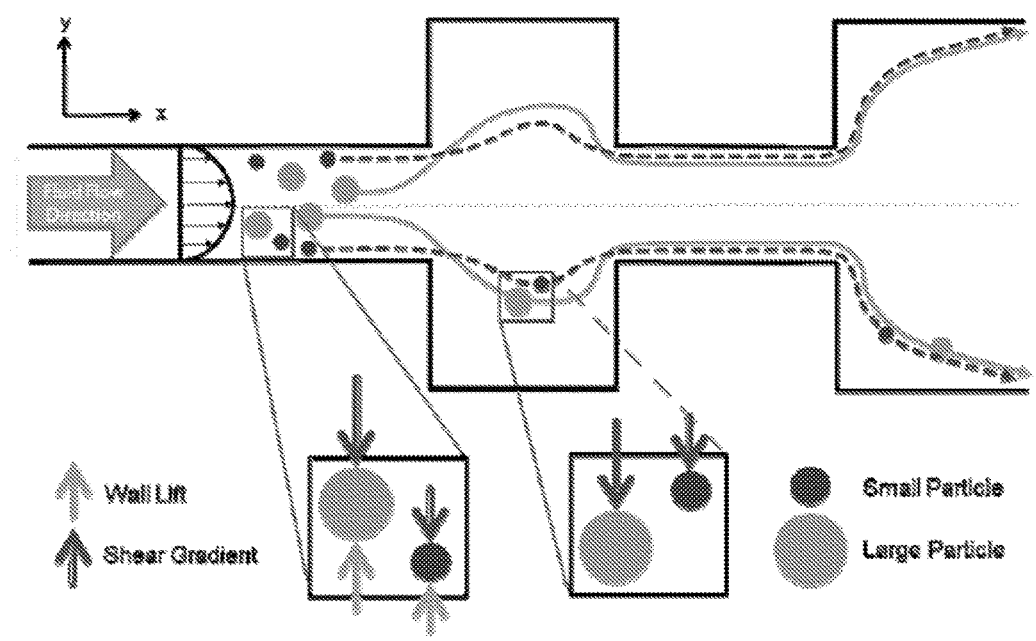
FIG. 15 shows a top view schematic of stage one, symmetric contraction expansion array (sCEA) for particle inertial focusing, according to embodiments of the present disclosure. Fluid flow is in the x-direction. Particles are randomly dispersed at the inlet. The particles are then focused to their respective equilibrium positions. Further focusing is achieved as particles enter expansion regions where shear lift forces dominate to pull particles closer the outer walls. At the outlet, two compact streamlines are observed close to the outer walls of the microchannel.

A multi-stage device was produced that separated cells by size, and isolated rare cells, such as circulating tumor cells in peripheral blood. The device included a combination of symmetric and asymmetric "contraction-expansion" array devices (sCEA and aCEA, respectively), which utilized a balance of inertial forces (inertial-lift forces vs. Dean drag force) to separate cells on size. The first stage focused cells into two distinct flow paths at the outer walls of a single microchannel. As shown in FIG. 15, randomly distributed cells in suspension or whole blood entered the microchannel. Within the contraction regions of stage 1, particles in suspension were subjected to a balance of counteracting lift forces—a wall lift force and a shear-gradient lift force. As a result, particles migrated to a unique equilibrium position that depended on particle diameter and was also weakly dependent on density. The wall lift force, $F_{WL}$, acted to push particles towards the centerline of the microchannel and scaled as, $$F_{WL} = \frac{f_L \rho U_m^2 a^6}{W^4}$$

The shear gradient lift force, $F_{SL}$, acted to push particles towards channel walls and scaled as, $$F_{SL} = \frac{f_L \rho U_m^2 a^3}{W}$$

where, $f_L$, a, and W are the dimensionless lift coefficient, particle diameter, and channel width. As shown in FIG. 15, particles were randomly dispersed at the inlet, were eventually ordered within their respective equilibrium position, refocused within the well, and focused in a compact streamline.

Figure 17:
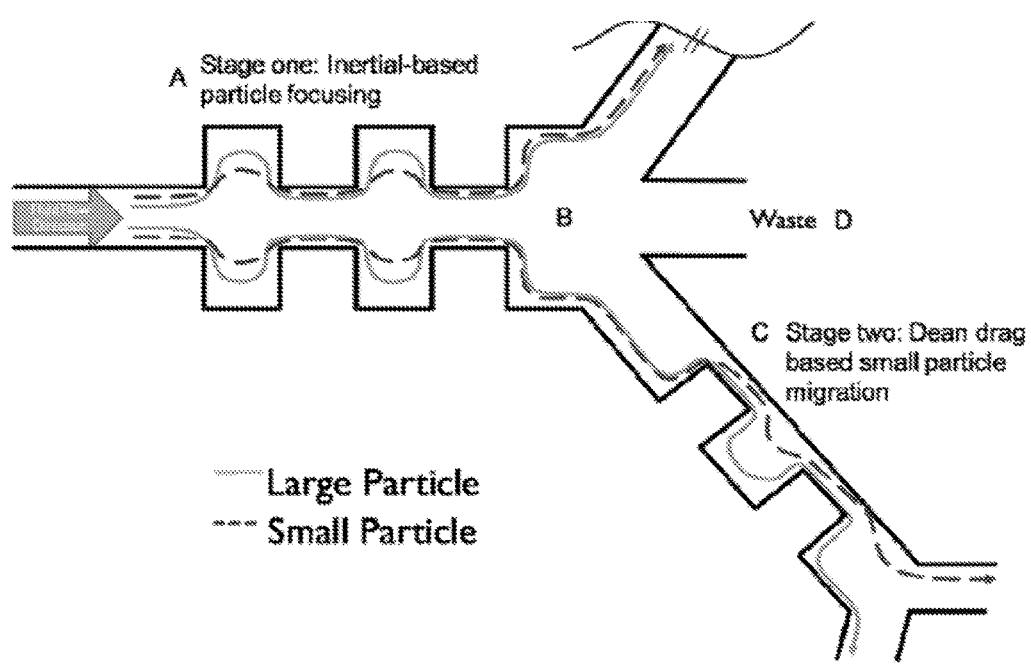
FIG. 17 shows a schematic of a multi-stage CEA device, according to embodiments of the present disclosure. The multi-stage CEA devise includes a sCEA connected in series to two aCEA devices, which are in parallel with each other, for sized based cell sorting. Sample, such as whole blood, is focused with inertial lift forces and dean drag forces and further purified through CD45 negative selection. Element A of the device is Stage 1: sCEA focuses most suspended cells to outer walls by inertial lift forces). Element B of the device includes a junction between Stage 1 and Stage 2. Element C of the device is Stage 2: Two parallel aCEA devices take intertially focused cells and utilizes Dean drag force to migrate small cells to a different equilibrium position. Element D of the device includes a resistive element used to maintain equal flow at device's bifurcation. Element E (not shown) of the device includes an anti-CD45 antibody reservoir used to capture white blood cells and further purify sample.

In Stage 2 of the device, both inertial lift ($F_{WL}+F_{SL}$) and Dean drag forces, $$F_D = 3\pi\mu U_{Dean} a$$

where $U_{Dean}$ was the transverse velocity by Dean flow, were used to separate particles based on size. As shown in FIG. 17, Stage 2 included a microchannel that had asymmetrical expansion and contraction regions. This was an asymmetric contraction expansion array (aCEA) that operated with or without a sheath focusing flow. The changes in the cross sectional area due to these expansion and contraction areas accelerated and decelerated the flow velocity and induced Dean-like flow. Cells were inertially focused toward Sidewall 1 upon being injected into Stage 2 and can be further focused with an additional sheath fluid if necessary. The net inertial lift force dominated larger-sized cells to Sidewall 1 and to a specific output. In contrast, a Dean-drag force dominated and directed smaller-sized particles to the opposite Sidewall 2 and to a different output.

An asymmetric CEA (aCEA) device was coupled to a symmetric CEA (sCEA) device described above, as shown in FIG. 17. The microfluidic device utilized a balance of inertial lift and Dean drag forces to focus cells into the desired equilibrium positions during fluid flow. In order to separate larger cells (e.g., cancer cells >15 μm) selectively, a two-stage process was used. As shown in FIG. 15, Stage 1 focused cells into a tight streamline along the outer microfluidic walls via a balance of shear gradient and wall inertial-lift forces, and Stage 2 utilized a Dean drag force to size separate the cells in the streamline prepared by Stage 1. The multi-stage device improved both processing throughput and filtration efficiency.

A single sCEA device, stage 1, was connected in series with two parallel aCEA devices, stage two. The sCEA devices inertially focused the side walls in stage 1, see Element A of the device shown in FIG. 17. At the end of stage 1, the flow was split into three outlets: two outlets leading into two separate aCEA devices in parallel and one waste outlet. When connecting the sCEA device to the two parallel aCEA devices an imbalance in resistance and pressure was observed at the waste outlet. To minimize this imbalance, a resistive element was used to balance flow between the collection and waste outlet of the first CEA, as shown in FIG. 17 (see Element D of the device shown in FIG. 17). In addition, a region directly connected to the collection output of stage 2 was included that was functionalized with a saturating concentration of anti-CD45 antibodies. The antibodies captured the white blood cells only, not cancer or other rare cells, due to specific binding, thus removing them from the processed sample. A high purity sample was obtained. Alternatively, a dielectrophoresis device can be used to remove white blood cells of comparable size to CTCs. Other embodiments of the devices can include different markers that would capture subpopulations of WBC's.

This device can be used to isolate rare cells, such as circulating tumor cells and other residual disease cells, in peripheral blood. It can also be used, in combination with Node-Pore Sensing technology, to perform CBCs and to screen isolated cells for specific markers indicating the cell's phenotype.

Example 4

A multistage CEA device that included a sCEA device coupled to an aCEA device as described above was tested. The sCEA device (stage 1) was 20-30 mm in length. The contraction regions of the sCEA device were 30-80 μm in width, 115-180 μm in length, and 65-80 μm in height. The expansion regions of the sCEA device were 90-240 μm in width, 115-180 μm in length, and 65-80 μm in height. Stage 2 (aCEA) was as described in Example 2 above. The range in dimensions provided flexibility when targeting different specific cell size thresholds.

The multistage device function was confirmed by running whole blood spiked with MCF-7 GFP breast cancer cells with a Millipore Guava Flowcytometer. Whole blood spiked with MCF-7 GFP breast cancer cells was injected into the device at a chosen rate of 180-200 μl/min in the sample inlet and phosphate buffered saline (PBS) solution was injected at a chosen rate of 200-250 μl/min in the buffer inlet.

Figure 19:
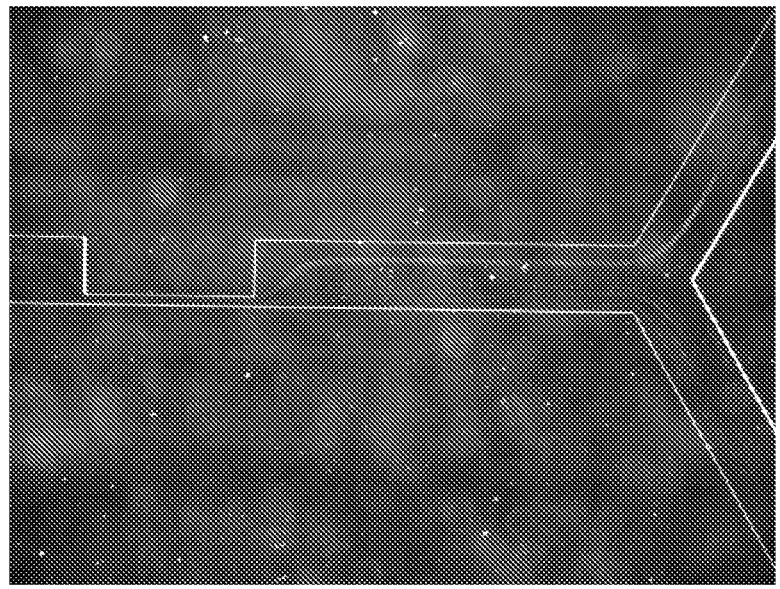
FIG. 19 shows an image of an experiment using diluted whole blood spiked with MCF-7 cells, according to embodiments of the present disclosure. Red blood cells (RBCs) exited the device through the bottom outlet to waste. MCF-7 cells exited through the top outlet for collection. The sample flow rate was 200 µl/min and a buffer flowrate of 200 µl/min.

FIG. 19 shows an image of an experiment using diluted whole blood spiked with MCF-7 cells. Red blood cells (RBCs) exited the device through the bottom outlet to waste. MCF-7 cells exited through the top outlet for collection. The sample flow rate was 200 μl/min and a buffer flow rate of 200 μl/min.

Figure 20:
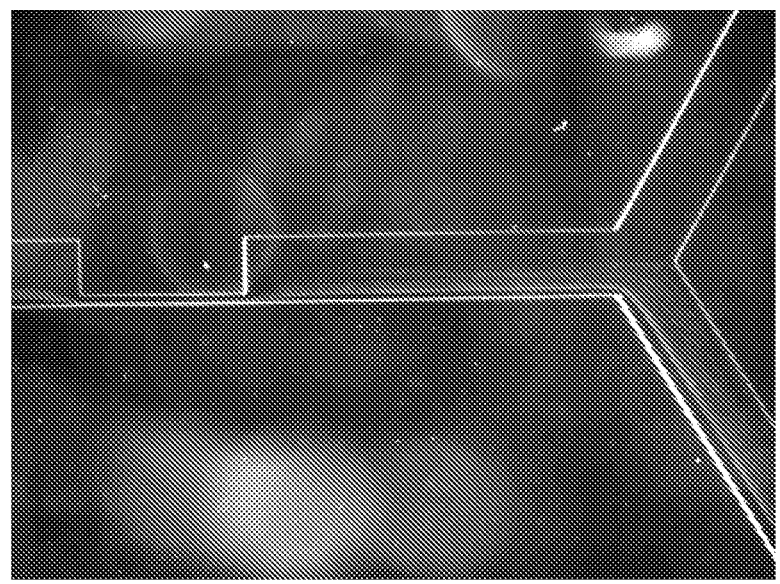
FIG. 20 shows an image of an experiment using diluted whole blood, according to embodiments of the present disclosure. Red blood cells (RBCs) exited the device through the bottom outlet to waste. The sample flow rate was 200 µl/min and a buffer flowrate of 200 µl/min.

FIG. 20 shows an image of an experiment using diluted whole blood. Red blood cells (RBCs) exited the device through the bottom outlet to waste. The sample flow rate was 200 μl/min and a buffer flow rate of 200 μl/min.

Example 5

A multistage CEA device that included a sCEA device coupled to an aCEA device as described above was tested. The sCEA device (stage 1) was 20-30 mm in length. The contraction regions of the sCEA device were 30-80 μm in width, 115-180 μm in length, and 65-80 μm in height. The expansion regions of the sCEA device were 90-240 μm in width, 115-180 μm in length, and 65-80 μm in height. Stage 2 (aCEA) was as described in Example 2 above. The range in dimensions provided flexibility when targeting different specific cell size thresholds.

The multistage device function was confirmed by running whole blood spiked with MCF-7 GFP breast cancer cells with a Millipore Guava Flowcytometer. Whole blood spiked with MCF-7 GFP breast cancer cells was injected into the device at a chosen rate of 180-200 μl/min in the sample inlet and phosphate buffered saline (PBS) solution was injected at a chosen rate of 200-250 μl/min in the buffer inlet.

As shown in FIGS. 21 to 35, experiments were performed in which 80,000 MCF-7 GFP cells were spiked into whole blood and processed through the multistage device at a flow rate of 180 μl/min and a buffer flow rate of 200 μl/min. Greater than 85% of MCF-7 GFP cells were recovered in collection. Approximately 10% of the cultured MCF-7 GFP cells may have had a cell diameter smaller than the threshold (12 μm) and can be found in the waste.

Figure 21:
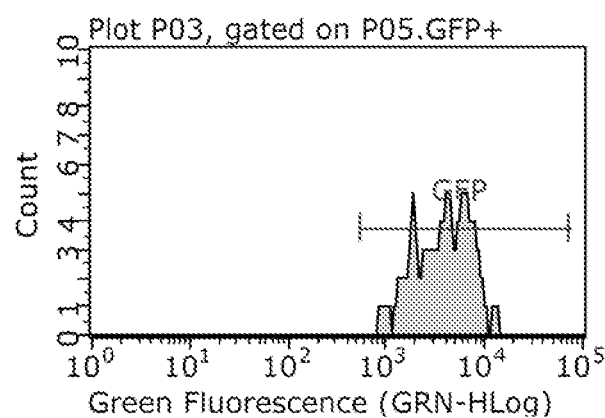
FIG. 21 shows a histogram of GFP Green fluorescence versus Count for device collection. Collection was analyzed with Guava Flow Cytometer. Well C01. Sample flowrate: 180 µl/min Buffer flowrate: 200 µl/min.

FIG. 21 shows a histogram of GFP Green fluorescence versus Count for device collection. Collection was analyzed with Guava Flow Cytometer. Well C01. Sample flowrate: 180 μl/min Buffer flowrate: 200 μl/min.

Figure 22:
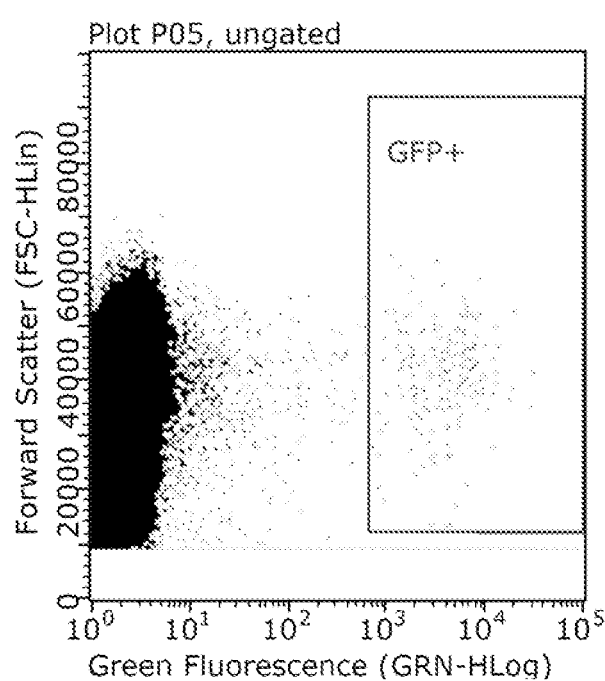
FIG. 22 shows a dot plot of GFP Green fluorescence versus Forward Scatter for device collection. Collection was analyzed with Guava Flow Cytometer. Well C01. Sample flowrate: 180 µl/min Buffer flowrate: 200 µl/min.

FIG. 22 shows a dot plot of GFP Green fluorescence versus Forward Scatter for device collection. Collection was analyzed with Guava Flow Cytometer. Well C01. Sample flowrate: 180 μl/min Buffer flowrate: 200 μl/min.

Figure 23:
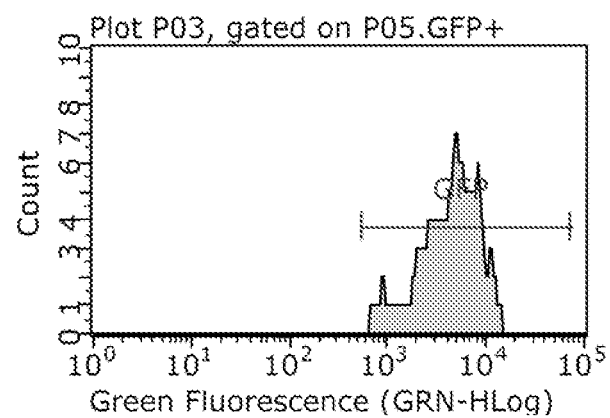
FIG. 23 shows a histogram of GFP Green fluorescence versus Count for device collection. Collection was analyzed with Guava Flow Cytometer. Well C02. Sample flowrate: 180 µl/min Buffer flowrate: 200 µl/min.

FIG. 23 shows a histogram of GFP Green fluorescence versus Count for device collection. Collection was analyzed with Guava Flow Cytometer. Well C02. Sample flowrate: 180 μl/min Buffer flowrate: 200 μl/min.

Figure 24:
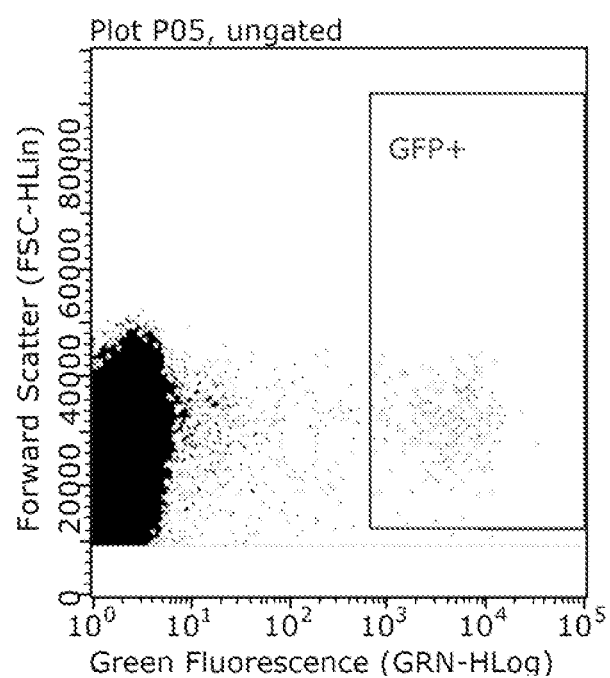
FIG. 24 shows a dot plot of GFP Green fluorescence versus Forward Scatter for device collection. Collection was analyzed with Guava Flow Cytometer. Well C02. Sample flowrate: 180 µl/min Buffer flowrate: 200 µl/min.

FIG. 24 shows a dot plot of GFP Green fluorescence versus Forward Scatter for device collection. Collection was analyzed with Guava Flow Cytometer. Well C02. Sample flowrate: 180 μl/min Buffer flowrate: 200 μl/min.

Figure 25:
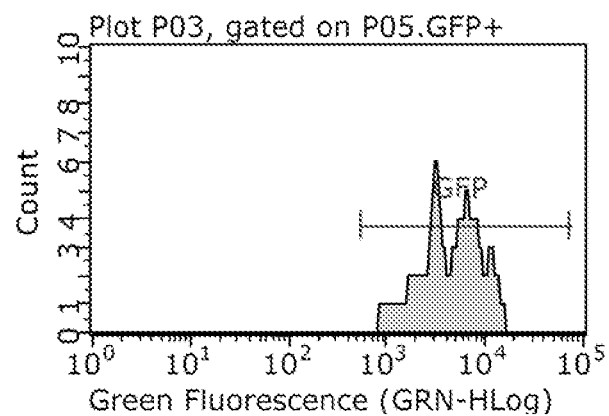
FIG. 25 shows a histogram of GFP Green fluorescence versus Count for device collection. Collection was analyzed with Guava Flow Cytometer. Well C03. Sample flowrate: 180 µl/min Buffer flowrate: 200 µl/min.

FIG. 25 shows a histogram of GFP Green fluorescence versus Count for device collection. Collection was analyzed with Guava Flow Cytometer. Well C03. Sample flowrate: 180 μl/min Buffer flowrate: 200 μl/min.

Figure 26:
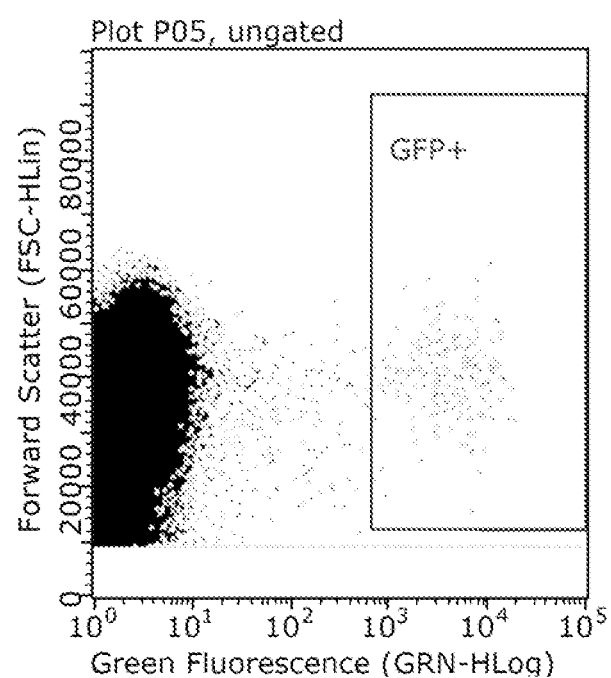
FIG. 26 shows a dor plot of GFP Green fluorescence versus Forward Scatter for device collection. Collection was analyzed with Guava Flow Cytometer. Well C03. Sample flowrate: 180 µl/min Buffer flowrate: 200 µl/min.

FIG. 26 shows a dot plot of GFP Green fluorescence versus Forward Scatter for device collection. Collection was analyzed with Guava Flow Cytometer. Well C03. Sample flowrate: 180 μl/min Buffer flowrate: 200 μl/min.

Figure 27:
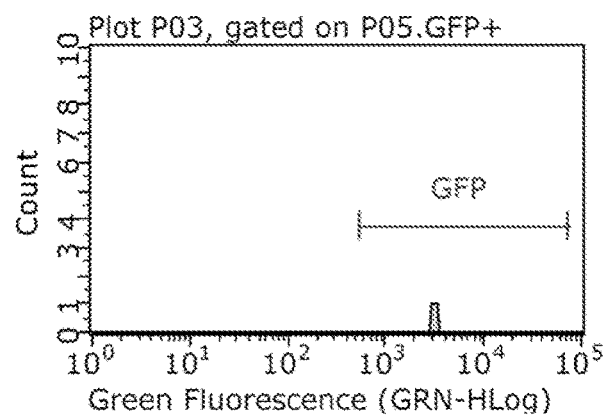
FIG. 27 shows a histogram of GFP Green fluorescence versus Count for device waste. Waste was analyzed with Guava Flow Cytometer. Well D01. Sample flowrate: 180 µl/min Buffer flowrate: 200 µl/min.

FIG. 27 shows a histogram of GFP Green fluorescence versus Count for device waste. Waste was analyzed with Guava Flow Cytometer. Well D01. Sample flowrate: 180 μl/min Buffer flowrate: 200 μl/min.

Figure 28:
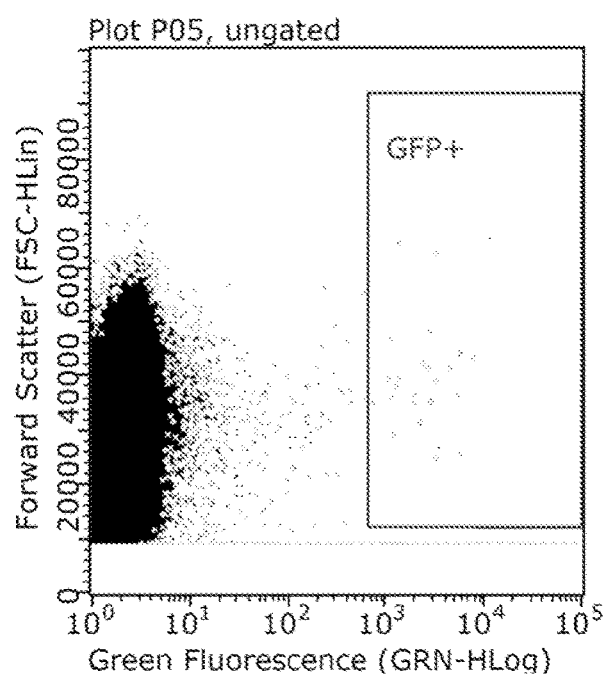
FIG. 28 shows a dot plot of GFP Green fluorescence versus Forward Scatter for device waste. Waste was analyzed with Guava Flow Cytometer. Well D01. Sample flowrate: 180 µl/min Buffer flowrate: 200 µl/min.

FIG. 28 shows a dot plot of GFP Green fluorescence versus Forward Scatter for device waste. Waste was analyzed with Guava Flow Cytometer. Well D01. Sample flowrate: 180 μl/min Buffer flowrate: 200 μl/min.

Figure 29:
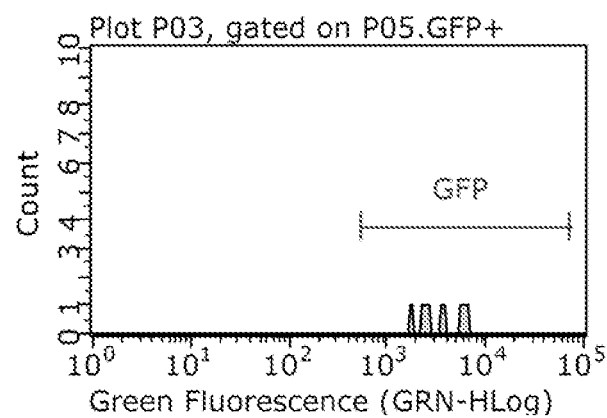
FIG. 29 shows a histogram of GFP Green fluorescence versus Count for device waste. Waste was analyzed with Guava Flow Cytometer. Well D02. Sample flowrate: 180 µl/min Buffer flowrate: 200 µl/min.

FIG. 29 shows a histogram of GFP Green fluorescence versus Count for device waste. Waste was analyzed with Guava Flow Cytometer. Well D02. Sample flowrate: 180 μl/min Buffer flowrate: 200 μl/min.

Figure 30:
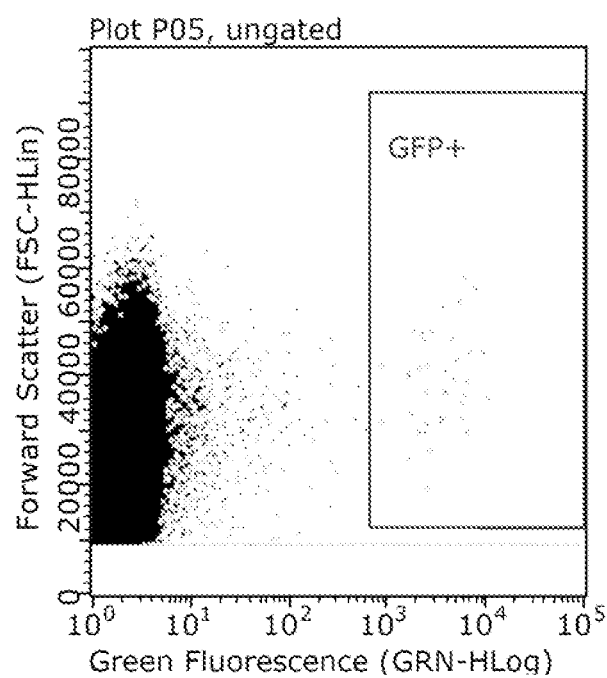
FIG. 30 shows a dot plot of GFP Green fluorescence versus Forward Scatter for device waste. Waste was analyzed with Guava Flow Cytometer. Well D02. Sample flowrate: 180 µl/min Buffer flowrate: 200 µl/min.

FIG. 30 shows a dot plot of GFP Green fluorescence versus Forward Scatter for device waste. Waste was analyzed with Guava Flow Cytometer. Well D02. Sample flowrate: 180 μl/min Buffer flowrate: 200 μl/min.

Figure 31:
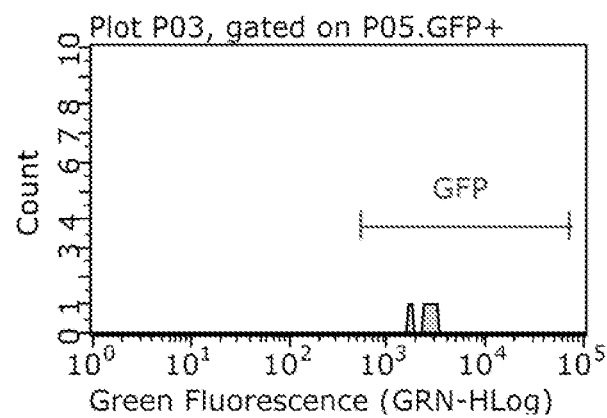
FIG. 31 shows a histogram of GFP Green fluorescence versus Count for device waste. Waste was analyzed with Guava Flow Cytometer. Well D03. Sample flowrate: 180 µl/min Buffer flowrate: 200 µl/min.

FIG. 31 shows a histogram of GFP Green fluorescence versus Count for device waste. Waste was analyzed with Guava Flow Cytometer. Well D03. Sample flowrate: 180 μl/min Buffer flowrate: 200 μl/min.

Figure 32:
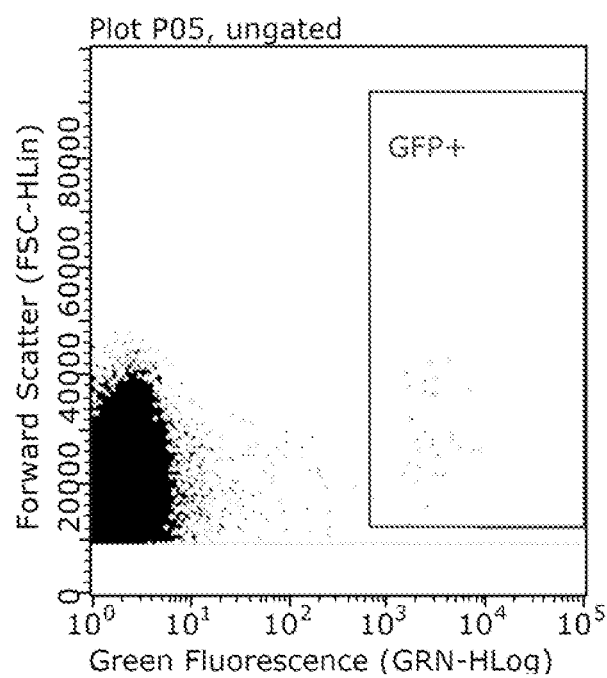
FIG. 32 shows a dot plot of GFP Green fluorescence versus Forward Scatter for device waste. Waste was analyzed with Guava Flow Cytometer. Well D03. Sample flowrate: 180 µl/min Buffer flowrate: 200 µl/min.

FIG. 32 shows a dot plot of GFP Green fluorescence versus Forward Scatter for device waste. Waste was analyzed with Guava Flow Cytometer. Well D03. Sample flowrate: 180 μl/min Buffer flowrate: 200 μl/min.

Figure 33:
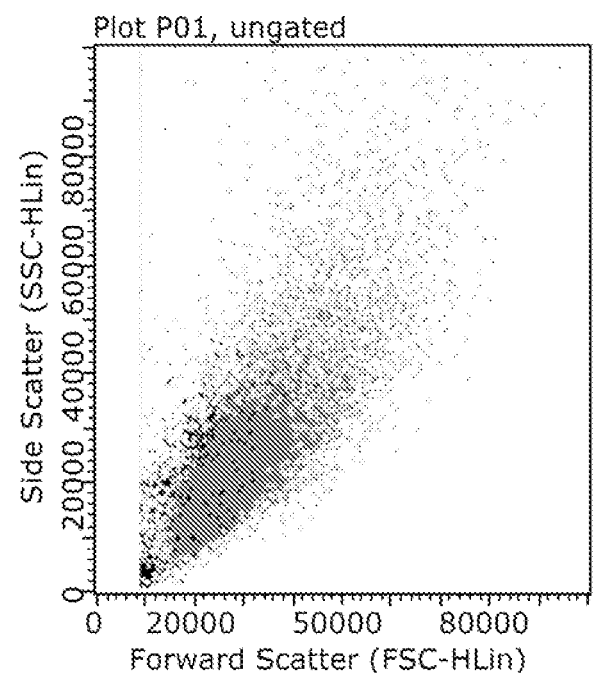
FIG. 33 shows a dot plot of Forward Scatter vs Side Scatter for MCF7-GFP cell florescence control. Control was analyzed with Guava Flow Cytometer.

FIG. 33 shows a dot plot of Forward Scatter vs Side Scatter for MCF7-GFP cell florescence control. Control was analyzed with Guava Flow Cytometer.

Figure 34:
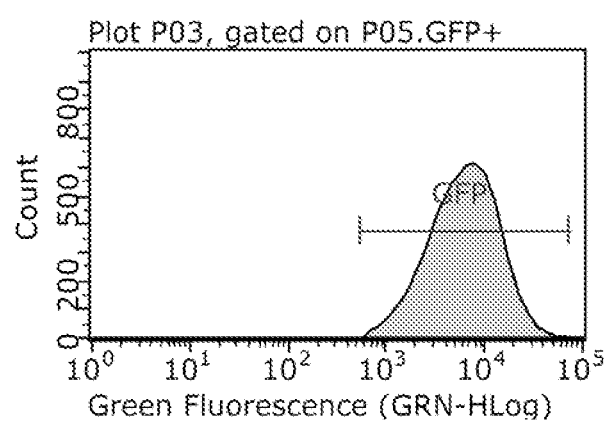
FIG. 34 shows a histogram of GFP Green fluorescence versus Count for MCF7-GFP cell florescence control. Control was analyzed with Guava Flow Cytometer.

FIG. 34 shows a histogram of GFP Green fluorescence versus Count for MCF7-GFP cell florescence control. Control was analyzed with Guava Flow Cytometer.

Figure 35:
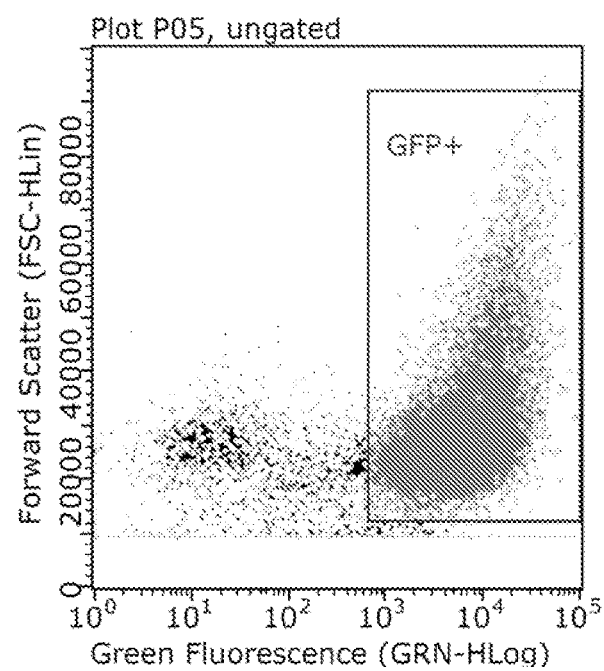
FIG. 35 shows a dot plot of GFP Green fluorescence versus Forward Scatter for MCF7-GFP cell florescence control. Control was analyzed with Guava Flow Cytometer.

FIG. 35 shows a dot plot of GFP Green fluorescence versus Forward Scatter for MCF7-GFP cell florescence control. Control was analyzed with Guava Flow Cytometer.

As shown in FIGS. 36 to 43, experiments were performed in which 800 MCF-7 GFP cells were spiked into 1 mL whole blood and processed through the multistage device at a flow rate of 200 μl/min and a buffer flow rate of 250 μl/min. Greater than 96% of MCF-7 GFP cells were recovered in collection. Approximately 10% of the cultured MCF-7 GFP cells may have a cell diameter smaller than the threshold (12 μm) and can be found in the waste.

Figure 36:
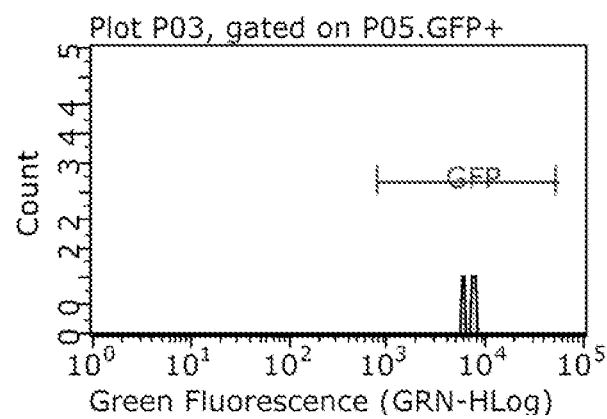
FIG. 36 shows a histogram of GFP Green fluorescence versus Count for device collection. Collection was analyzed with Guava Flow Cytometer. Collection bottom right. Sample flowrate: 200 µl/min Buffer flowrate: 250 µl/min. 800 MCF-7 GFP cells spiked in 1 mL of whole blood.

FIG. 36 shows a histogram of GFP Green fluorescence versus Count for device collection. Collection was analyzed with Guava Flow Cytometer. Collection bottom right. Sample flowrate: 200 μl/min Buffer flowrate: 250 μl/min. 800 MCF-7 GFP cells spiked in 1 mL of whole blood.

Figure 37:
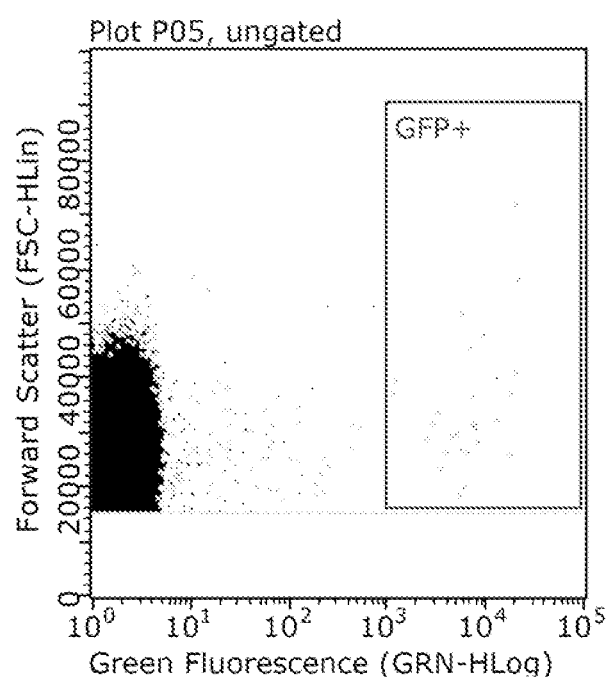
FIG. 37 shows a dot plot of GFP Green fluorescence versus Forward Scatter for device collection. Collection was analyzed with Guava Flow Cytometer. Collection bottom right. Sample flowrate: 200 µl/min Buffer flowrate: 250 µl/min. 800 MCF-7 GFP cells spiked in 1 mL of whole blood.

FIG. 37 shows a dot plot of GFP Green fluorescence versus Forward Scatter for device collection. Collection was analyzed with Guava Flow Cytometer. Collection bottom right. Sample flowrate: 200 μl/min Buffer flowrate: 250 μl/min. 800 MCF-7 GFP cells spiked in 1 mL of whole blood.

Figure 38:
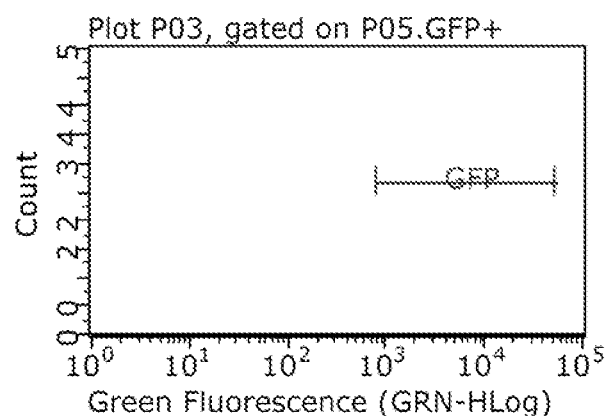
FIG. 38 shows a histogram of GFP Green fluorescence versus Count for device waste. Waste was analyzed with Guava Flow Cytometer. Waste bottom right. Sample flowrate: 200 µl/min Buffer flowrate: 250 µl/min. 800 MCF-7 GFP cells spiked in 1 mL of whole blood.

FIG. 38 shows a histogram of GFP Green fluorescence versus Count for device waste. Waste was analyzed with Guava Flow Cytometer. Waste bottom right. Sample flowrate: 200 μl/min Buffer flowrate: 250 μl/min. 800 MCF-7 GFP cells spiked in 1 mL of whole blood.

Figure 39:
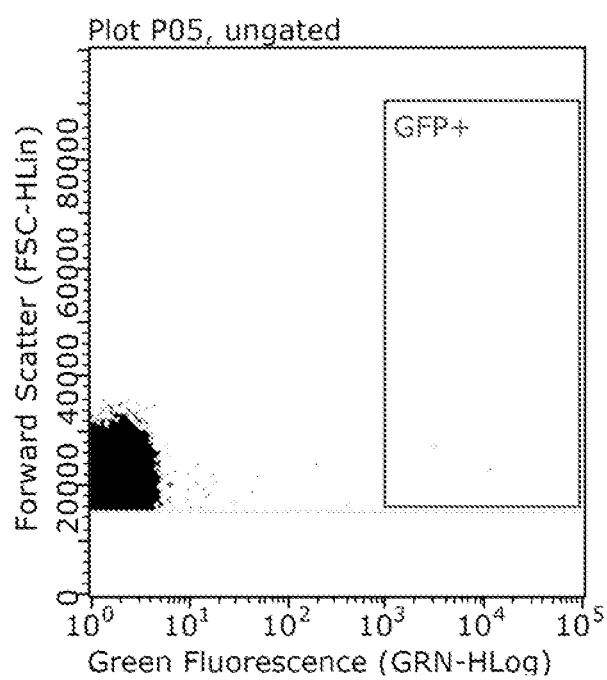
FIG. 39 shows a dot plot of GFP Green fluorescence versus Forward Scatter for device waste. Waste was analyzed with Guava Flow Cytometer. Waste bottom right.

FIG. 39 shows a dot plot of GFP Green fluorescence versus Forward Scatter for device waste. Waste was analyzed with Guava Flow Cytometer. Waste bottom right. Sample flowrate: 200 μl/min Buffer flowrate: 250 μl/min. 800 MCF-7 GFP cells spiked in 1 mL of whole blood.

FIG. 40 shows a histogram of GFP Green fluorescence versus Count for device collection. Collection was analyzed with Guava Flow Cytometer. Collection bottom top. Sample flowrate: 200 μl/min Buffer flowrate: 250 μl/min. 800 MCF-7 GFP cells spiked in 1 mL of whole blood.

FIG. 41 shows a dot plot of GFP Green fluorescence versus Forward Scatter for device collection. Collection was analyzed with Guava Flow Cytometer. Collection bottom top. Sample flowrate: 200 μl/min Buffer flowrate: 250 μl/min. 800 MCF-7 GFP cells spiked in 1 mL of whole blood.

FIG. 42 shoes a histogram of GFP Green fluorescence versus Count for device waste. Waste was analyzed with Guava Flow Cytometer. Waste right top. Sample flowrate: 200 μl/min Buffer flowrate: 250 μl/min. 800 MCF-7 GFP cells spiked in 1 mL of whole blood.

FIG. 43 shows a dot plot of GFP Green fluorescence versus Forward Scatter for device waste. Waste was analyzed with Guava Flow Cytometer. Waste right top. Sample flowrate: 200 μl/min Buffer flowrate: 250 μl/min. 800 MCF-7 GFP cells spiked in 1 mL of whole blood.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A device for separating constituents in a fluid sample, the device comprising:
    a microfluidic conduit configured to carry a flow of a fluid sample and comprising two or more separation elements, each separation element comprising a first region and a second region, wherein the first region has a cross-sectional area less than a cross-sectional area of the second region; and
    a flow resistive element in fluid communication with the microfluidic conduit in a region between two adjacent separation elements.

2. The device of claim 1, wherein the first region and the second region of each separation element are arranged symmetrically about a longitudinal axis of the microfluidic conduit.

3. The device of claim 1, wherein the first region and the second region of each separation element are arranged asymmetrically about a longitudinal axis of the microfluidic conduit.

4. The device of claim 1, wherein the two or more separation elements are arranged in series.

5. The device of claim 1, wherein the two or more separation elements are arranged in parallel.

6. The device of claim 1, wherein the two or more separation elements are arranged in series and in parallel.

7. The device of claim 1, wherein the device comprises:
    a first separation element, wherein the first region and the second region of the first separation element are arranged asymmetrically about a longitudinal axis of the microfluidic conduit; and
    a second separation element arranged in series with the first separation element, wherein the first region and the second region of the second separation element are arranged asymmetrically about a longitudinal axis of the microfluidic conduit, and
    wherein the flow resistive element is in fluid communication with the microfluidic conduit in a region between the first and second separation elements.

8. The device of claim 1, wherein the device comprises:
    a first separation element, wherein the first region and the second region of the first separation element are arranged symmetrically about a longitudinal axis of the microfluidic conduit;
    a second separation element arranged in series with the first separation element, wherein the first region and the second region of the second separation element are arranged asymmetrically about a longitudinal axis of the microfluidic conduit; and
    a third separation element arranged in series with the first separation element and in parallel with the second separation element, wherein the first region and the second region of the third separation element are arranged asymmetrically about a longitudinal axis of the microfluidic conduit; and
    wherein the flow resistive element is in fluid communication with the microfluidic conduit in a region between the first separation element and the second and third separation elements.

9. The device of claim 1, wherein the flow resistive element comprises an elongated conduit with a cross-sectional area less than the cross-sectional area of the second region.

10. The device of claim 1, wherein the flow resistive element comprises an elongated serpentine conduit.

11. The device of claim 1, further comprising a specific binding region in fluid communication with a downstream end of the microfluidic conduit.

12. The device of claim 11, wherein the specific binding region comprises a surface comprising a specific binding member in contact with the flow of the fluid sample.

13. The device of claim 12, wherein the specific binding member comprises an antibody.

14. The device of claim 13, wherein the antibody specifically binds to leukocytes.

15. The device of claim 1, wherein the first region has a conduit width ranging from 25 µm to 100 µm.

16. The device of claim 1, wherein the second region has a conduit width ranging from 250 µm to 500 µm.

17. The device of claim 1, further comprising an inlet in fluid communication with an upstream end of the microfluidic conduit.

18. The device of claim 1, further comprising an outlet in fluid communication with a downstream end of the microfluidic conduit.

19. The device of claim 1, wherein the flow resistive element is configured to provide resistance to the flow of the fluid sample to maintain a balanced and equal flow through the microfluidic conduit.

20. The device of claim 1, wherein the two or more separation elements comprise a first separation element and a second separation element, wherein the first separation element is upstream to the second separation element and comprises two outlets, and wherein one outlet is in fluid communication with an inlet of the second separation element and the other outlet is in fluid communication with the flow resistive element.

21. The device of claim 1, wherein the flow resistive element is between a first outlet and a second outlet of a separation element.

22. The device of claim 1, wherein the first region has a conduit width ranging from 1 µm to 1000 µm.

23. The device of claim 1, wherein the second region has a conduit width ranging from 1 µm to 2000 µm.

24. A system for separating constituents in a fluid sample, the system comprising:

(a) a device comprising:
 (i) a microfluidic conduit configured to carry a flow of a fluid sample and comprising two or more separation elements, each separation element comprising a first region and a second region, wherein the first region has a cross-sectional area less than a cross-sectional area of the second region; and
 (ii) a flow resistive element in fluid communication with the microfluidic conduit in a region between two adjacent separation elements; and
(b) a pressure source.

25. The system of claim 24, wherein the pressure source comprises a fluid pump.

26. The system of claim 24, further comprising a detector.

27. The system of claim 26, wherein the detector comprises a fluorescence detector, a camera, a complementary metal-oxide semiconductor (CMOS), a charge-coupled device (CCD), an intensified charge-coupled device (ICCD), a Coulter counter, or a node-pore sensing device.

28. A method of separating constituents in a fluid sample, the method comprising:
 passing a fluid sample comprising a plurality of constituents through a device comprising:
  a microfluidic conduit comprising two or more separation elements, each separation element comprising a first region and a second region, wherein the first region has a cross-sectional area less than a cross-sectional area of the second region; and
  a flow resistive element in fluid communication with the microfluidic conduit in a region between two adjacent separation elements,
 to separate a population of constituents from the constituents in the fluid sample.

29. The method of claim 28, further comprising collecting the population of constituents from an outlet in fluid communication with a downstream end of the microfluidic conduit.

30. The method of claim 28, wherein the population of constituents has an average diameter greater than the average diameter of the constituents in the fluid sample.

31. The method of claim 28, wherein the population of constituents has an average diameter less than the average diameter of the constituents in the fluid sample.

32. The method of claim 28, wherein the fluid sample comprises a non-biological sample.

33. The method of claim 28, wherein the fluid sample comprises whole blood.

34. The method of claim 33, wherein the population of constituents comprises circulating tumor cells.

35. The method of claim 28, further comprising characterizing the constituents that pass through the microfluidic conduit.

36. The method of claim 28, wherein the passing comprises flowing the fluid sample through the microfluidic conduit at a flow rate of 100 µL/min or more.

37. A kit comprising:
(a) a device according to claim 1; and
(b) a packaging configured to contain the device.

38. The kit of claim 37, further comprising a buffer.

* * * * *